(12) United States Patent
Assmann et al.

(10) Patent No.: US 6,235,765 B1
(45) Date of Patent: May 22, 2001

(54) BENZIMIDAZOLE DERIVATIVES

(75) Inventors: Lutz Assmann, Eutin; Albrecht Marhold, Leverkusen; Klaus Stenzel, Düsseldorf; Martin Kugler, Leichlingen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/490,482

(22) Filed: Jan. 24, 2000

Related U.S. Application Data

(62) Division of application No. 09/227,809, filed as application No. PCT/EP96/01435 on Jan. 11, 1999, now Pat. No. 6,080,776, which is a division of application No. 08/930,767, filed on Oct. 3, 1997, now Pat. No. 5,925,663.

(30) Foreign Application Priority Data

Apr. 13, 1995 (DE) ................................................ 195 13 990

(51) Int. Cl.$^7$ .................... A01N 43/52; C07D 401/12; C07D 401/06; C07D 401/04
(52) U.S. Cl. ................ 514/395; 514/394; 548/302.1; 548/304.7
(58) Field of Search .................................... 514/394, 395; 548/302.1, 304.7

(56) References Cited

U.S. PATENT DOCUMENTS 5,656,649   8/1997   Lunkenheimer et al. .

FOREIGN PATENT DOCUMENTS 9404509   3/1994   (WO) .
9411352   5/1994   (WO) .

*Primary Examiner*—Patricia L. Morris
(74) *Attorney, Agent, or Firm*—Norris McLaughlin & Marcus

(57) ABSTRACT

Novel benzimidazole derivatives of the formula

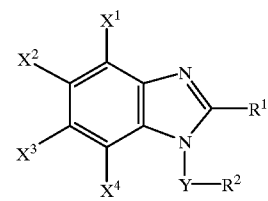

(I)

in which $R^1$, $R^2$, $X^1$, $X^2$, $X^3$, $X^4$ and Y are each as defined in the description, and acid addition salts and metal salt complexes thereof, a process for preparing these compounds and their use as microbicides in crop protection and in the protection of materials.

6 Claims, No Drawings

BENZIMIDAZOLE DERIVATIVES

This application is a divisional of U.S. Ser. No. 09/227,809, filed Jan. 11, 1999, now U.S. Pat. No. 6,080,776, issued Jun. 27, 2000, which is a divisional of U.S. Ser. No. 08/930,767, filed Oct. 3, 1997, now U.S. Pat. No. 5,925,663, issued Jul. 20, 1999, which is a 371 of PCT/EP96/01435 filed Jan. 4, 1996.

The present invention relates to novel benzimidazole derivatives, to a process for their preparation and to their use as microbicides in crop protection and in the protection of materials.

It is already known that certain benzimidazole derivatives have fungicidal properties (cf. DE-A 4 139 950 and EP-A 0 517 476). Thus, for example 2-cyano-1-dimethylaminosulphonyl-6,6,7,7-tetrafluoro-[1,4]dioxino[2,3-f]benzimidazole and 2-cyano-6,6-difluoro-1-dimethylaminosulphonyl-[1,3]dioxolo[4,5-f]benzimidazole can be used for controlling fungi. The activity of these compounds is good, but in some cases leaves something to be desired at low application rates.

This invention, accordingly, provides novel benzimidazole derivatives of the formula

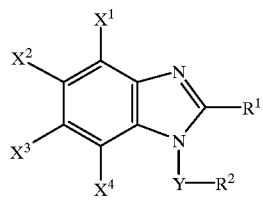

(I)

in which $X^1$, $X^2$, $X^3$ and $X^4$ independently of one another each represent hydrogen, halogen, cyano, nitro, alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphonyl, optionally substituted cycloalkyl, hydroxycarbonyl, alkylcarbonyl, alkoxycarbonyl, cycloalkylcarbonyl, cycloalkoxycarbonyl, represent

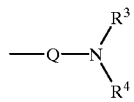

or —Z—$R^5$ in which $R^3$ and $R^4$ independently of one another each represent hydrogen, alkyl, halogenoalkyl, alkoxyalkyl, alkylcarbonyl, optionally substituted aryl, optionally substituted arylcarbonyl, optionally substituted arylsulphonyl, optionally substituted arylaminocarbonyl or optionally substituted arylmethylsulphonyl or $R^3$ and $R^4$ together with the nitrogen atom that they are attached to represent an optionally alkyl-substituted heterocyclic ring which may contain an additional oxygen atom or an aklylimino group, Q represents a direct bond or a carbonyl group, $R^5$ represents optionally substituted aryl or represents optionally substituted heterocyclyl and Z represents a direct bond, represents $CH_2$, O, S, SO, $SO_2$, CO or an azo group or represents —CO—O—, where the oxygen atom is linked to the aryl or heterocyclyl radical, or represents —$SO_2$—O—, where the sulphur atom is linked to the aryl or heterocyclyl radical, or represents —S—$CH_2$—$SO_2$—, where the sulphur atom of the thio group is linked to the aryl or heterocyclyl radical, or $X^2$ and $X^3$ together represent an optionally substituted alkylene chain having 3 or 4 members wherein one or two (non-adjacent) carbon atoms may be replaced by oxygen atoms, $R^1$ represents cyano or the groupings

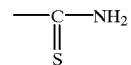

or

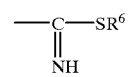

in which $R^6$ represents alkyl, halogenoalkyl or optionally halogen- and/or halogenoalkyl-substituted benzyl, $R^2$ represents optionally substituted heterocyclyl and Y represents a direct bond, represents —$CH_2$—, —$CH_2$—$CH_2$—, —CO—, —$SO_2$—, —CO—O— or —SO—O— where in the case of the last two groups the carbon atom or the sulphur atom is linked to the nitrogen atom of the imidazole ring, and acid addition salts and metal salt complexes thereof.

Furthermore, it was found that benzimidazole derivatives of the formula (I) and acid addition salts and metal salt complexes thereof are obtained when cyanobenzimidazoles of the formula

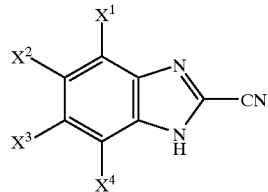

(II)

in which $X^1$, $X^2$, $X^3$ and $X^4$ are each as defined above are reacted with halides of the formula

Hal—Y—$R^2$ (III)

in which $R^2$ and Y are each as defined above and

Hal represents chlorine or bromine, if appropriate in the presence of an acid binder and if appropriate in the presence of a diluent, and the resulting benzimidazoles of the formula

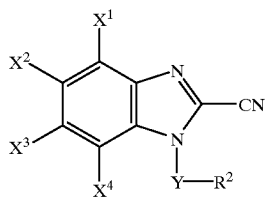

(I-a)

in which

R², Y, X¹, X², X³ and X⁴ are each as defined above are, if appropriate, either a) reacted with hydrogen sulphide in the presence of an acid binder and in the presence of a diluent, or b) reacted with a sulphur compound of the formula

H—S—R⁶ (IV)

in which

R⁶ is as defined above in the presence of an acid binder and in the presence of a diluent, and an acid or a metal salt is, if appropriate, added to the resulting compounds of the formula (I).

Finally, it was found that the benzimidazole derivatives of the formula (I) and acid addition salts and metal salt complexes thereof have very good microbicidal properties and can be used in crop protection and in the protection of materials.

Surprisingly, the compounds according to the invention have better fungicidal activity than 2-cyano-1-dimethylaminosulphonyl-6,6,7,7-tetrafluoro-[1,4]dioxino-[2,3-f]benzimidazole and 2-cyano-6,6-difluoro-1-dimethylaminosulphonyl-[1,3]-dioxolo[4,5-f]benzimidazole, which are compounds of the prior art of a similar structure and of the same direction of action.

A general definition of the compounds according to the invention is given by the formula (I).

X¹, X², X³ and X⁴ independently of one another each preferably represent hydrogen, fluorine, chlorine, bromine, iodine, cyano, nitro, straight-chain or branched alkyl having 1 to 8 carbon atoms, straight-chain or branched halogenoalkyl having 1 to 6 carbon atoms and 1 to 13 identical or different halogen atoms, straight-chain or branched alkoxy having 1 to 8 carbon atoms, straight-chain or branched halogenoalkoxy having 1 to 6 carbon atoms and 1 to 13 identical or different halogen atoms, straight-chain or branched alkylthio having 1 to 8 carbon atoms, straight-chain or branched halogenoalkylthio having 1 to 6 carbon atoms and 1 to 13 identical or different halogen atoms, straight-chain or branched alkylsulphinyl having 1 to 8 carbon atoms, straight-chain or branched halogenoalkylsulphinyl having 1 to 6 carbon atoms and 1 to 13 identical or different halogen atoms, straight-chain or branched alkylsulphonyl having 1 to 8 carbon atoms, straight-chain or branched halogenoalkylsulphonyl having 1 to 6 carbon atoms and 1 to 13 identical or different halogen atoms, cycloalkyl having 3 to 6 carbon atoms which is optionally mono- to pentasubstituted by identical or different substituents from the group consisting of halogen and alkyl having 1 to 4 carbon atoms, represent hydroxycarbonyl, alkylcarbonyl having 1 to 6 carbon atoms in the straight-chain or branched alkyl moiety, alkoxycarbonyl having 1 to 6 carbon atoms in the straight-chain or branched alkoxy moiety, cycloalkylcarbonyl having 3 to 6 carbon atoms in the cycloalkyl moiety, cycloalkoxycarbonyl having 3 to 6 carbon atoms in the cycloalkyl moiety, represent

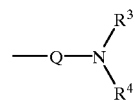

or —Z—R⁵.

R³ and R⁴ independently of one another each preferably represent hydrogen, straight-chain or branched alkyl having 1 to 6 carbon atoms, straight-chain or branched halogenoalkyl having 1 to 6 carbon atoms and 1 to 13 identical or different halogen atoms, straight-chain or branched alkoxyalkyl having 1 to 4 carbon atoms in the alkoxy moiety and 1 to 4 carbon atoms in the alkyl moiety, alkylcarbonyl having 1 to 6 carbon atoms in the straight-chain or branched alkyl moiety, aryl having 6 to 10 carbon atoms, arylcarbonyl having 6 to 10 carbon atoms in the aryl moiety, arylsulphonyl having 6 to 10 carbon atoms, arylaminocarbonyl having 6 to 10 carbon atoms in the aryl moiety or represent arylmethylsulphonyl having 6 to 10 carbon atoms in the aryl moeity, it being possible for each of the abovementioned aryl radicals to be mono- to trisubstituted by identical or different substituents from the group consisting of halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and halogenoalkylsulphonyl having 1 to 4 carbon atoms and 1 to 5 identical or different halogen atoms.

R³ and R⁴ together with the nitrogen atom that they are attached to additionally preferably represent a heterocyclic ring having 5 or 6 ring members which is optionally mono- to trisubstituted by alkyl having 1 to 4 carbon atoms and which may contain an additional oxygen atom or a $C_1$–$C_4$-alkylimino group.

Q preferably represents a direct bond or represents a carbonyl group.

R⁵ preferably represents aryl having 6 to 10 carbon atoms, it being possible for each of these radicals to be mono- to trisubstituted by identical or different substituents from the group consisting of halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and halogenoalkylsulphonyl having 1 to 4 carbon atoms and 1 to 5 identical or different halogen atoms, or $R^5$ preferably represents a saturated or unsaturated heterocyclyl radical having 5 or 6 ring members and 1 to 3 heteroatoms such as nitrogen, oxygen and/or sulphur, it being possible for these radicals to be mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 3 carbon atoms in the alkoxy moiety, cycloalkyl having 3 to 6 carbon atoms, cyano and nitro.

Z preferably represents a direct bond and also represents $CH_2$, O, S, SO, $SO_2$, CO or an azo group, or preferably represents —CO—O—, where the oxygen atom is linked to the aryl or heterocyclyl radical, or preferably represents —$SO_2$—O—, where the sulphur atom is linked to the aryl or heterocyclyl radical, or preferably represents —S—$CH_2$—$SO_2$—, where the sulphur atom of the thio group is linked to the aryl or heterocyclyl radical.

$X^2$ and $X^3$ together also preferably represent an alkylene chain having 3 or 4 members which is optionally mono- to hexasubstituted by halogen, alkyl having 1 to 4 carbon atoms and/or halogenoalkyl having 1 to 4 carbon atoms and 1 to 9 halogen atoms and in which one or two (non-adjacent) carbon atoms may be replaced by oxygen atoms.

$R^1$ preferably represents cyano or the groupings

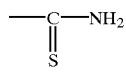

or

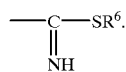

$R^6$ preferably represents straight-chain or branched alkyl having 1 to 4 carbon atoms, straight-chain or branched halogenoalkyl having 1 to 4 carbon atoms and 1 to 9 identical or different halogen atoms or represents benzyl which is optionally mono- to trisubstituted by identical or different substituents from the group consisting of halogen and halogenoalkyl having 1 or 2 carbon atoms and 1 to 5 identical or different halogen atoms.

$R^2$ preferably represents a saturated or unsaturated, optionally benzo-fused heterocyclyl radical having 5 or 6 ring members and 1 to 3 heteroatoms such as nitrogen, oxygen and/or sulphur, it being possible for these radicals to be mono- to trisubstituted by identical or different substituents from the group consisting of halogen, cyano, nitro, hydroxyl, amino, formyl, carboxy, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, alkylcarbonylamino having 1 to 4 carbon atoms in the alkyl group, hydroxyiminoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety and halogenoalkylcarbonyloxy having 1 to 4 carbon atoms in the halogenoalkyl group and 1 to 5 identical or different halogen atoms, it being possible for the heterocyclyl radicals to contain oxo groups.

Y preferably represents a direct bond, represents $CH_2$, $CH_2$—$CH_2$, CO, $SO_2$, —CO—O— or —SO—O—, where in the case of the last two groups the carbon atom or the sulphur atom is linked to the nitrogen atom of the imidazole ring.

$X^1$, $X^2$, $X^3$ and $X^4$ independently of one another each particularly preferably represent hydrogen, fluorine, chlorine, bromine, iodine, cyano, nitro, straight-chain or branched alkyl having 1 to 6 carbon atoms, halogenoalkyl having 1 or 2 carbon atoms and 1 to 5 fluorine, chlorine and/or bromine atoms, straight-chain or branched alkoxy having 1 to 6 carbon atoms, halogenoalkoxy having 1 or 2 carbon atoms and 1 to 5 fluorine, chlorine and/or bromine atoms, straight-chain or branched alkylthio having 1 to 6 carbon atoms, halogenoalkylthio having 1 or 2 carbon atoms and 1 to 5 fluorine, chlorine and/or bromine atoms, straight-chain or branched alkylsulphinyl having 1 to 6 carbon atoms, halogenoalkylsulphinyl having 1 or 2 carbon atoms and 1 to 5 fluorine, chlorine and/or bromine atoms, straight-chain or branched alkylsulphonyl having 1 to 6 carbon atoms, halogenoalkylsulphonyl having 1 or 2 carbon atoms and 1 to 5 fluorine, chlorine and/or bromine atoms, cycloalkyl having 3 to 6 carbon atoms which is optionally mono- to trisubstituted by identical or different substituents from the group consisting of fluorine, chlorine, bromine, methyl and ethyl, represents hydroxycarbonyl, alkylcarbonyl having 1 to 4 carbon atoms in the straight-chain or branched alkyl moiety, alkoxycarbonyl having 1 to 4 carbon atoms in the straight-chain or branched alkoxy moiety, cycloalkylcarbonyl having 3 to 6 carbon atoms in the cycloalkyl moiety, cycloalkoxycarbonyl having 3 to 6 carbon atoms in the cycloalkyl moiety, represents

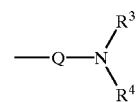

or —Z—$R^5$.

$R^3$ and $R^4$ independently of one another each particularly preferably represent hydrogen, straight-chain or branched alkyl having 1 to 4 carbon atoms, halogenoalkyl having 1 or 2 carbon atoms and 1 to 5 fluorine, chlorine and/or bromine atoms, straight-chain or branched alkoxyalkyl having 1 to 3 carbon atoms in the alkoxy moiety and 1 to 3 carbon atoms in the alkyl moiety, alkylcarbonyl having 1 to 4 carbon atoms in the straight-chain or branched alkyl moiety, phenyl, phenylcarbonyl, phenylsulphonyl, phenylaminocarbonyl or phenylmethylsulphonyl, it being possible for each of the abovementioned phenyl radicals to be mono- to trisubstituted by identical or different substituents from the group consisting of fluorine, chlorine, bromine, cyano, nitro, alkyl having 1 or 2 carbon atoms, alkoxy having 1 or 2 carbon atoms, alkylthio having 1 or 2 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, halogenoalkylthio having 1 or 2 carbon atoms and 1 to 5 fluorine, chlorine and/or bromine atoms, alkylsulphinyl having 1 or 2 carbon atoms, alkylsulphonyl having 1 or 2 carbon atoms, halogenoalkylsulphinyl having 1 or 2 carbon atoms and 1 to 5 fluorine, chlorine and/or bromine atoms and halogenoalkylsulphonyl having 1 or 2 carbon atoms and 1 to 5 fluorine, chlorine and/or bromine atoms.

$R^3$ and $R^4$ together with the nitrogen atom that they are attached to additionally particularly preferably represent a saturated heterocyclic ring having 5 or 6 ring members which is optionally mono- to trisubstituted by methyl and/or ethyl and in which one carbon atom of the ring may be replaced by oxygen or methylimino.

Q particularly preferably represents a direct bond or a carbonyl group.

$R^5$ particularly preferably represents phenyl which may be mono- to trisubstituted by identical or different substituents from the group consisting of fluorine, chlorine, bromine, cyano, nitro, alkyl having 1 or 2 carbon atoms, alkoxy having 1 or 2 carbon atoms, alkylthio having 1 or 2 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, halogenoalkylthio having 1 or 2 carbon atoms and 1 to 5 fluorine, chlorine and/or bromine atoms, alkylsulphinyl having 1 or 2 carbon atoms, alkylsulphonyl having 1 or 2 carbon atoms, halogenoalkylsulphinyl having 1 or 2 carbon atoms and 1 to 5 fluorine, chlorine and/or bromine atoms and halogenoalkylsulphonyl having 1 or 2 carbon atoms and 1 to 5 fluorine, chlorine and/or bromine atoms, or $R^5$ particularly preferably represents a saturated or unsaturated heterocyclyl radical having 5 or 6 ring members and 1 to 3 heteroatoms such as nitrogen, oxygen and/or sulphur, it being possible for these radicals to be mono- to trisubstituted by identical or different substituents from the group consisting of fluorine, chlorine, bromine, alkyl having 1 or 2 carbon atoms, alkoxy having 1 or 2 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, alkoxycarbonyl having 1 or 2 carbon atoms in the alkoxy moiety, cycloalkyl having 3 to 6 carbon atoms, cyano and nitro.

Z particularly preferably represents a direct bond and $CH_2$, O, S, SO, $S_2$, CO or an azo group, or represents —CO—O—, where the oxygen atom is linked to the phenyl or heterocyclyl radical, or represents —$SO_2$—O—, where the sulphur atom is linked to the phenyl or heterocyclyl radical, or represents —S—$CH_2$—$SO_2$—, where the sulphur atom of the thio group is linked to the phenyl or heterocyclyl radical.

$X^2$ and $X^3$ together additionally particularly preferably represent an alkylene chain having 3 or 4 members which is optionally mono- to hexasubstituted by fluorine, chlorine, methyl and/or trifluoromethyl and in which one or two (non-adjacent) carbon atoms may be replaced by oxygen.

$R^1$ particularly preferably represents cyano or the groupings

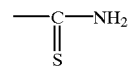

or

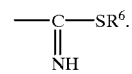

$R^6$ particularly preferably represents straight-chain or branched alkyl having 1 to 4 carbon atoms, straight-chain or branched halogenoalkyl having 1 to 4 carbon atoms and 1 to 5 fluorine, chlorine and/or bromine atoms or represents benzyl which is optionally mono- or disubstituted by identical or different substituents from the group consisting of fluorine, chlorine and trifluoromethyl.

$R^2$ particularly preferably represents a saturated or unsaturated, optionally benzo-fused heterocyclyl radical having 5 or 6 ring members and 1 to 3 hetero atoms such as nitrogen, oxygen and/or sulphur, it being possible for these radicals to be mono- to trisubstituted by identical or different substituents from the group consisting of fluorine, chlorine, bromine, cyano, nitro, hydroxyl, amino, formyl, carboxy, carbamoyl, thiocarbamoyl, alkyl having 1 to 4 carbon atoms, alkoxy having 1 to 4 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, alkoxycarbonyl having 1 or 2 carbon atoms in the alkoxy moiety, cycloalkyl having 3 to 6 carbon atoms, halogenoalkylsulphinyl having 1 or 2 carbon atoms and 1 to 5 fluorine, chlorine and/or bromine atoms, halogenoalkylsulphonyl having 1 or 2 carbon atoms and 1 to 5 fluorine, chlorine and/or bromine atoms, alkylamino having 1 or 2 carbon atoms, hydroxyalkylamino having 1 or 2 carbon atoms, dialkylamino having 1 to 2 carbon atoms in each alkyl group, alkylcarbonyl having 1 or 2 carbon atoms in the alkyl moiety, alkylcarbonylamino having 1 to 3 carbon atoms in the alkyl moiety, hydroxyiminoalkyl having 1 or 2 carbon atoms in the alkyl moiety, alkoximinoalkyl having 1 or 2 carbon atoms in the alkoxy moiety and 1 or 2 carbon atoms in the alkyl moiety, alkylcarbonyloxy having 1 or 2 carbon atoms in the alkyl group and halogenoalkylcarbonyloxy having 1 or 2 carbon atoms in the halogenoalkyl group and 1 to 5 fluorine, chlorine and/or bromine atoms, it being possible for the heterocyclyl radicals to contain one or two oxo groups.

Y particularly preferably represents a direct bond, represents $CH_2$, $CH_2$—$CH_2$, CO, $SO_2$, —CO—O— or —SO—O— where in the case of the last two groups the carbon atom or the sulphur atom is linked to the nitrogen atom of the imidazole ring.

$X^1$, $X^2$, $X^3$ and $X^4$ independently of one another each very particularly preferably represent hydrogen, fluorine, chlorine, bromine, cyano, nitro, represent methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, acetyl, acetyloxy, methoxycarbonyl, ethoxycarbonyl, cyclopropyl, cyclohexyl, represent

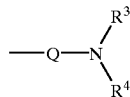

or —Z—$R^5$.

$R^3$ and $R^4$ independently of one another each very particularly preferably represent hydrogen, methyl, ethyl, n-propyl, isopropyl or phenyl.

$R^3$ and $R^4$ together with the nitrogen atom that they are attached to additionally very particularly preferably represent pyrrolidinyl, piperidinyl, morpholinyl or 4-methyl-piperazinyl.

Q very particularly preferably represents a direct bond or represents a carbonyl group.

$R^5$ very particularly preferably represents phenyl which may be mono- to trisubstituted by identical or different substituents from the group consisting of fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, difluoromethylsulphinyl and trifluoromethylsulphonyl, or $R^5$ very particularly preferably represents pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridinyl, pyrimidinyl, pyrazinyl or pyridazinyl, it being possible for these radicals to be mono- to trisubstituted by identical or different substituents from the group consisting of fluorine, chlorine, methyl, methoxy, trifluoromethyl, trifluoromethoxy and trifluoromethoxy.

Z very particularly preferably represents a direct bond and represents $CH_2$, O, S, SO, $SO_2$, CO or an azo group, or represents —CO—O—, where the oxygen atom is linked to the phenyl or heterocyclyl radical, or represents —$SO_2$—O—, where the sulphur atom is linked to the phenyl or heterocyclyl radical, or represents —S—$CH_2$—$SO_2$—, where the sulphur atom of the thio group is linked to the phenyl or heterocyclyl radical.

$X^2$ and $X^3$ together additionally very particularly preferably represent the groupings —O—$CF_2$—O—, —O—$CF_2$—CHF—O—, —O—CHF—CHF—O—, O—$CF_2$—$CF_2$—O—, —O—$CF_2$—CFCl—O—, —O—CFCl—CFCl—O—, —O—$CF_2$—$CF_2$— or —$CF_2$—$CF_2$—O—.

$R^1$ very particularly preferably represents cyano or the groupings

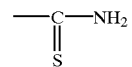

or

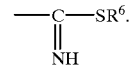

$R^6$ very particularly preferably represents methyl, ethyl, isopropyl, trichloromethyl, trifluoromethyl or benzyl.

$R^2$ very particularly preferably represents pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridinyl, pyrimidinyl, pyrazinyl, pyridazinyl, benzofuryl, benzothienyl, quinolyl or the radicals of the formulae

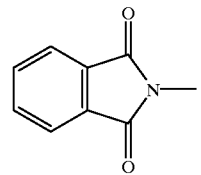

or

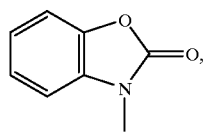

it being possible for these radicals to be mono- to trisubstituted by identical or different substituents from the group consisting of fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, methylcarbonylamino, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and ethoxyiminoethyl.

Y very particularly preferably represents a direct bond, represents $CH_2$, $CH_2$—$CH_2$, Co, $SO_2$, —CO—O— or —SO—O—, where in the case of the last two groups the carbon atom or the sulphur atom is linked to the nitrogen of the imidazole ring.

Preferred compounds according to the invention are also the addition products of acids and those benzimidazole derivatives of the formula (I) in which $R^1$, $R^2$, $X^1$, $X^2$, $X^3$, $X^4$ and Y each have those meanings which have been mentioned as being preferred for these radicals.

The acids which can be subjected to an addition reaction preferably include hydrohalic acids, such as, for example, hydrochloric acid and hydrobromic acid, in particular hydrochloric acid, furthermore phosphoric acid, nitric acid, mono- and bifunctional carboxylic acids and hydrocarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid and 1,5-naphthalenedisulphonic acid, and also saccharin and thiosaccharin.

Other preferred compounds according to the invention are adducts of salts of metals of main groups II to IV and sub-groups I and II and IV to VIII of the Periodic Table of the Elements and those benzimidazole derivatives of the formula (I) in which $R^1$, $R^2$, $X^1$, $X^2$, $X^3$, $X^4$ and Y each have those meanings which have been mentioned as being preferred for these radicals.

Salts of copper, zinc, manganese, magnesium, tin, iron and nickel are particularly preferred in this context. Suitable anions of these salts are those which are derived from acids which lead to physiologically acceptable adducts. Particularly preferred acids of this type are, in this context, the hydrohalic acids, such as, for example, hydrochloric acid and hydrobromic acid, furthermore phosphoric acid, nitric acid and sulphuric acid.

Examples of compounds according to the invention which may be mentioned are the benzimidazole derivatives listed in the tables below.

TABLE I

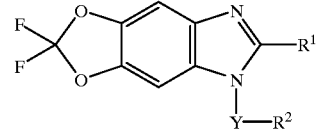

(I-b)

| $R^1$ | $R^2$—Y |
|---|---|
| —CN | 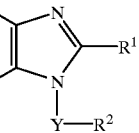 |
| —CN | 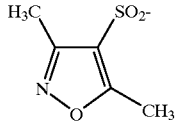 |
| —CN | 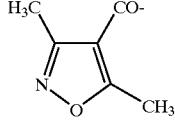 |
| —CN | 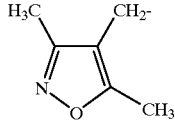 |
| —CN | 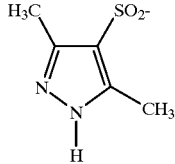 |

TABLE I-continued

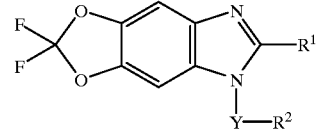

(I-b)

| $R^1$ | $R^2$—Y |
|---|---|
| —CN | 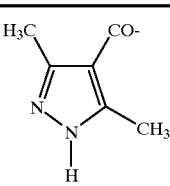 |
| —CN | 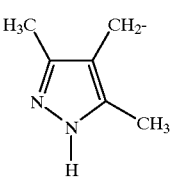 |
| —CN | 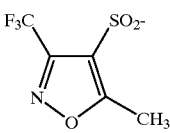 |
| —CN | 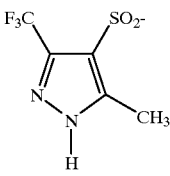 |
| —CN | 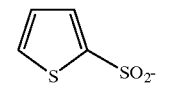 |
| —CN | 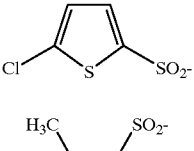 |
| —CN | 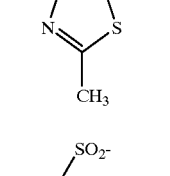 |
| —CN | 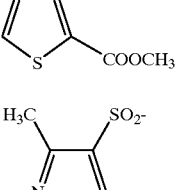 |

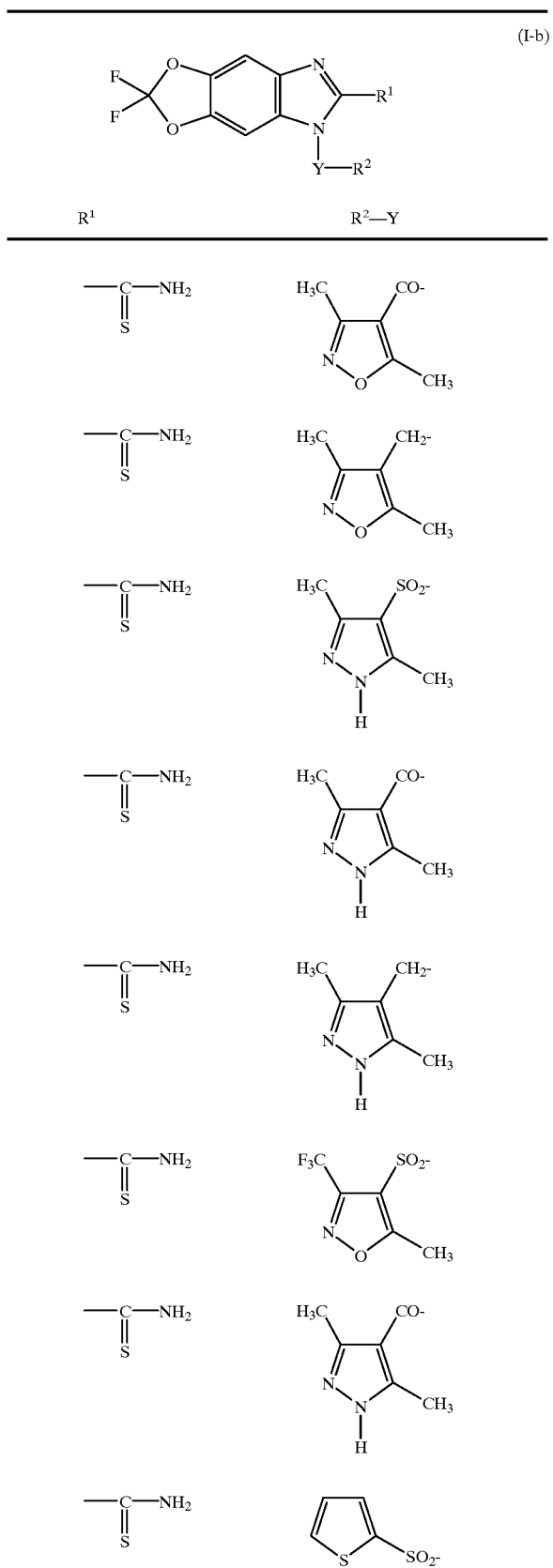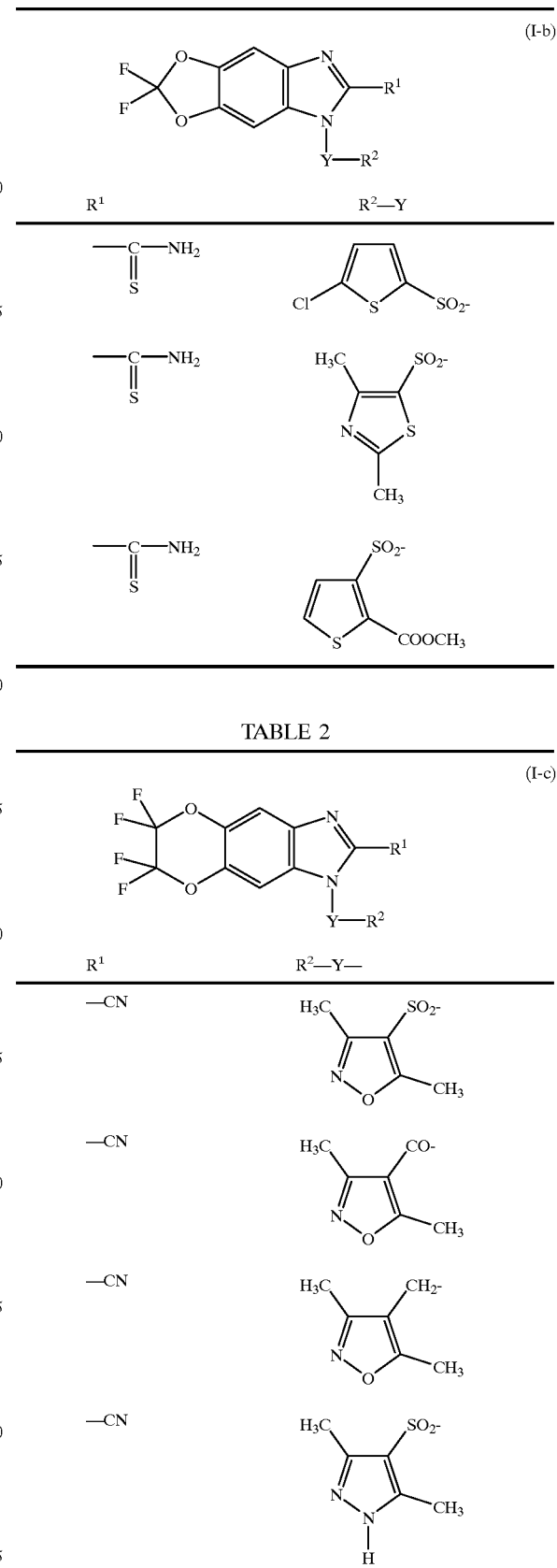

TABLE 2-continued (I-c)

[Structure: tetrafluoro-dioxino-benzimidazole with R¹ and Y-R² substituents]

| R¹ | R²—Y— |
|---|---|
| —CN | 3,5-dimethyl-1H-pyrazol-4-yl-CO- |
| —CN | 3,5-dimethyl-1H-pyrazol-4-yl-CH₂- |
| —CN | 3-CF₃-5-methyl-isoxazol-4-yl-SO₂- |
| —CN | 3-CF₃-5-methyl-1H-pyrazol-4-yl-SO₂- |
| —CN | thiophen-2-yl-SO₂- |
| —CN | 5-chloro-thiophen-2-yl-SO₂- |
| —CN | 4-methyl-2-methyl-thiazol-5-yl-SO₂- |
| —CN | 2-(COOCH₃)-thiophen-3-yl-SO₂- |
| —C(=S)NH₂ | 3,5-dimethyl-isoxazol-4-yl-SO₂- |
| —C(=S)NH₂ | 3,5-dimethyl-isoxazol-4-yl-CO- |
| —C(=S)NH₂ | 3,5-dimethyl-isoxazol-4-yl-CH₂- |
| —C(=S)NH₂ | 3,5-dimethyl-1H-pyrazol-4-yl-SO₂- |
| —C(=S)NH₂ | 3,5-dimethyl-1H-pyrazol-4-yl-CO- |
| —C(=S)NH₂ | 3,5-dimethyl-1H-pyrazol-4-yl-CH₂- |
| —C(=S)NH₂ | 3-CF₃-5-methyl-isoxazol-4-yl-SO₂- |
| —C(=S)NH₂ | 3-CF₃-5-methyl-1H-pyrazol-4-yl-SO₂- |
| —C(=S)NH₂ | thiophen-2-yl-SO₂- |

TABLE 2-continued
(I-c)
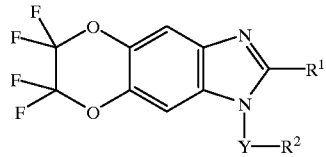
| R¹ | R²—Y— |
|---|---|
| 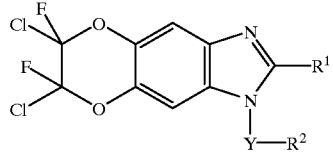 | 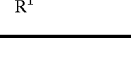 |
| 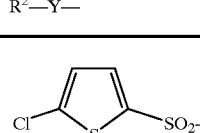 | 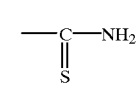 |
| 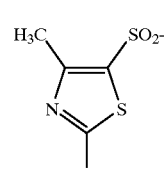 | 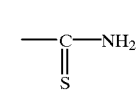 |
TABLE 3
(I-d)
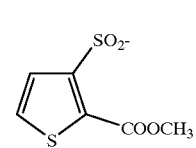
| R¹ | R²—Y |
|---|---|
| —CN |  |
| —CN | 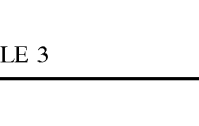 |
| —CN | 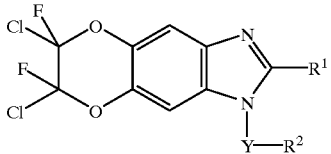 |
TABLE 3-continued
(I-d)
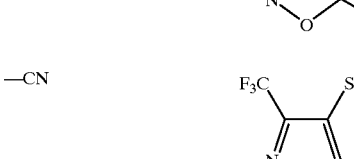
| R¹ | R²—Y |
|---|---|
| —CN |  |
| —CN | 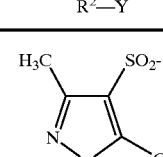 |
| —CN |  |
| —CN | 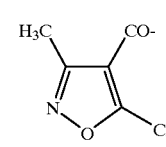 |
| —CN |  |
| —CN | 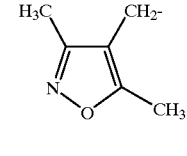 |
| —CN | (5-chlorothiophene-2-sulfonyl) |
| —CN | (2-methyl-4-methylthiazole-5-sulfonyl) |

TABLE 3-continued
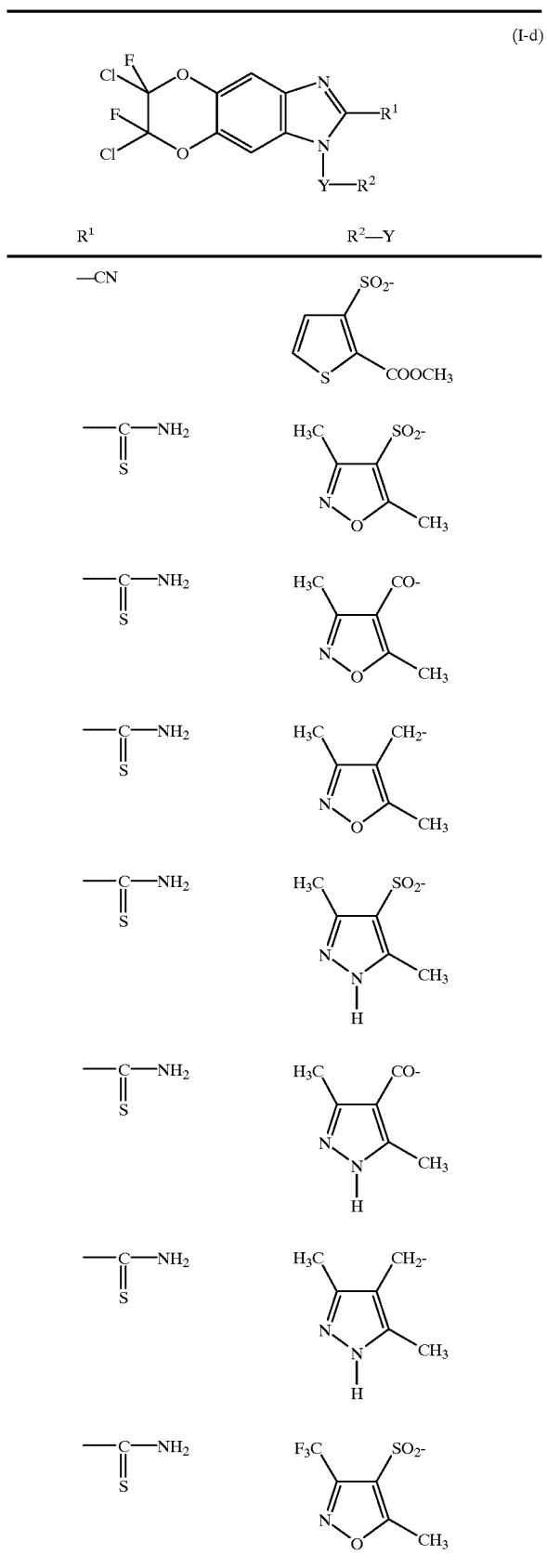
TABLE 3-continued
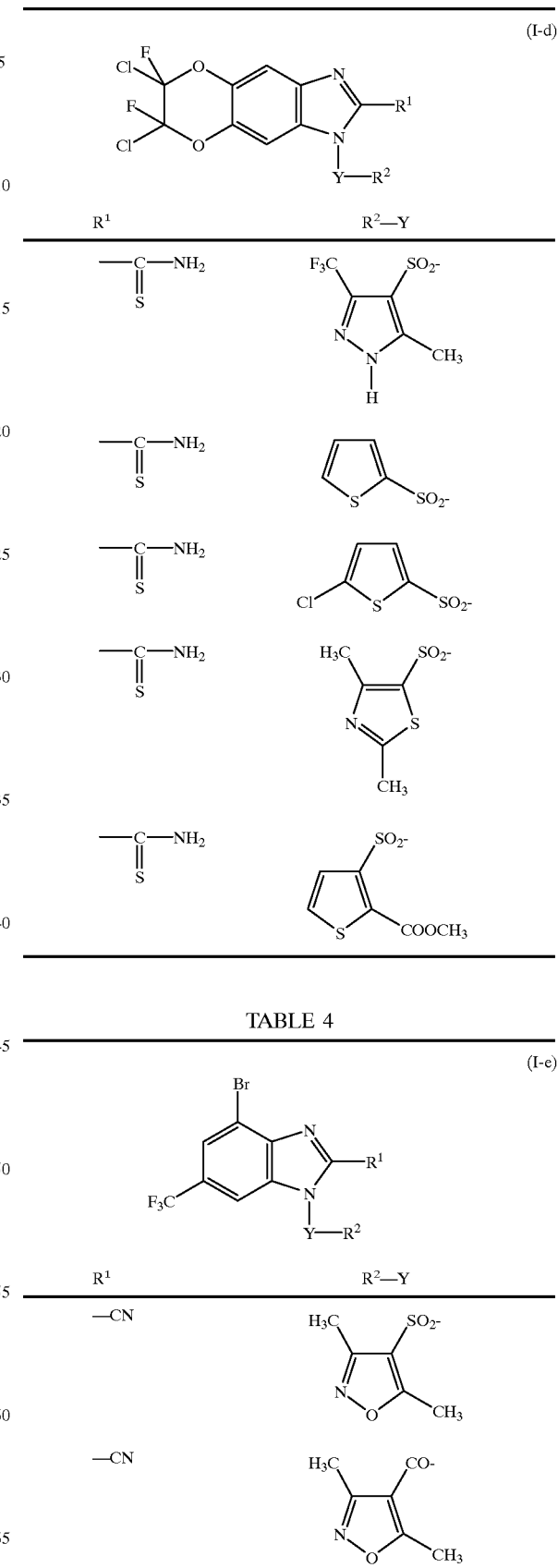

TABLE 4-continued
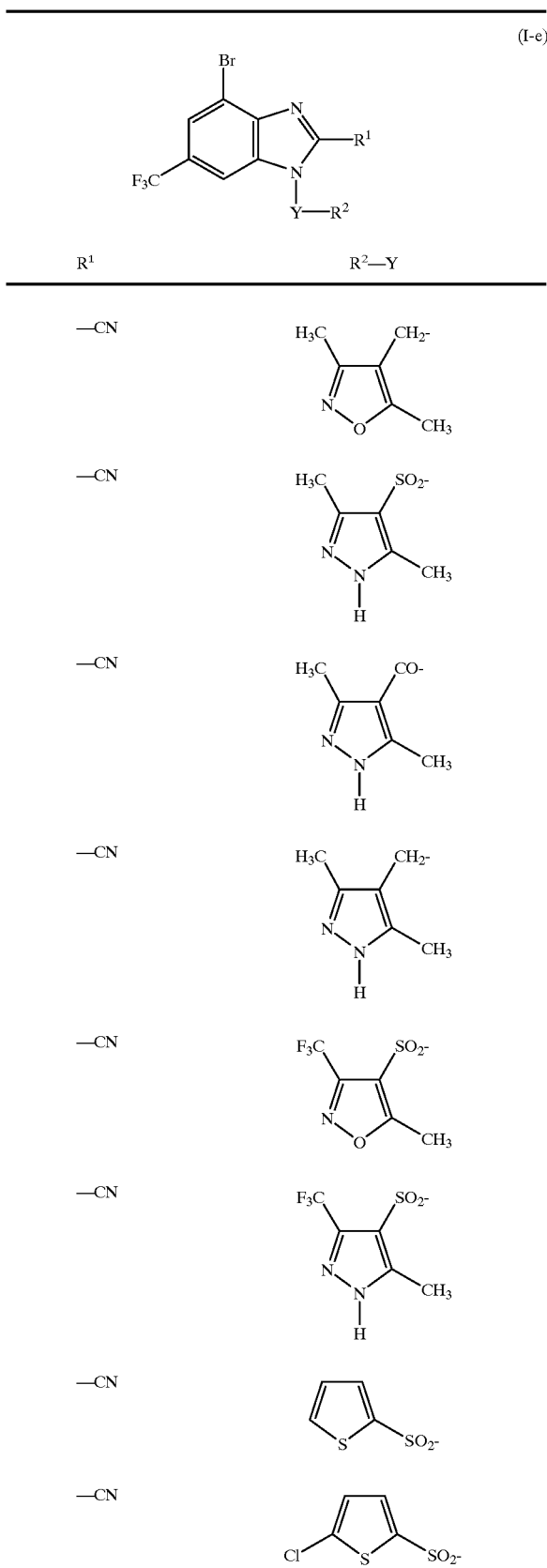
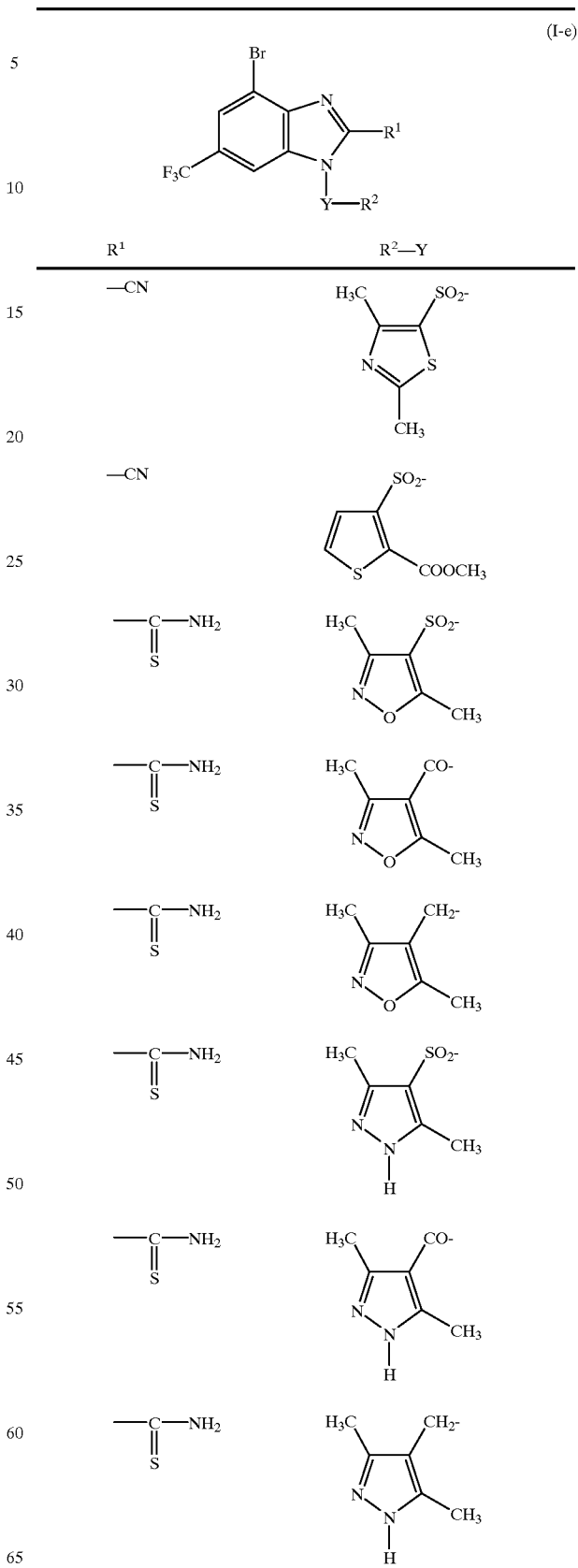

TABLE 4-continued
(I-e)
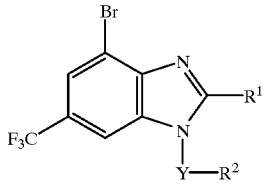
| R¹ | R²—Y |
|---|---|
| 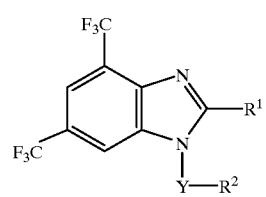 | 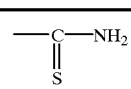 |
| 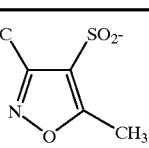 | 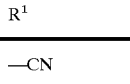 |
| 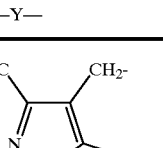 | 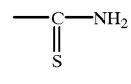 |
| 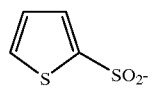 |  |
| 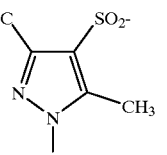 | 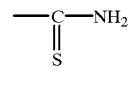 |
TABLE 5
(I-f)
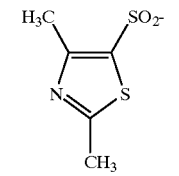
| R¹ | R²—Y— |
|---|---|
| —CN |  |
| —CN | 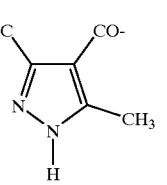 |
| —CN | 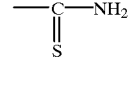 |
| —CN | 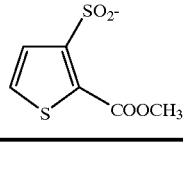 |
| —CN |  |
| —CN | 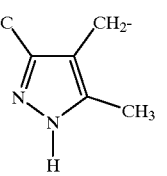 |
| —CN | 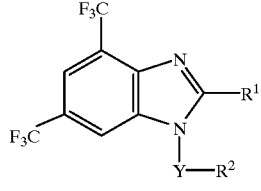 |
| —CN | 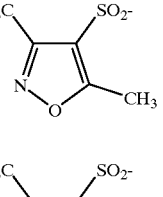 |
| —CN |  |
| —CN | 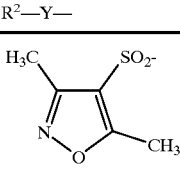 |
| —CN |  |

TABLE 5-continued (I-f)

[Structure: 4,6-bis(trifluoromethyl)benzimidazole with R¹ at 2-position and Y-R² on N1]

| R¹ | R²—Y— |
|---|---|
| —CN | 2,4-dimethylthiazol-5-yl-SO₂- |
| —CN | 2-(methoxycarbonyl)thiophen-3-yl-SO₂- |
| —C(=S)NH₂ | 3,5-dimethylisoxazol-4-yl-SO₂- |
| —C(=S)NH₂ | 3,5-dimethylisoxazol-4-yl-CO- |
| —C(=S)NH₂ | 3,5-dimethylisoxazol-4-yl-CH₂- |
| —C(=S)NH₂ | 3,5-dimethyl-1H-pyrazol-4-yl-SO₂- |
| —C(=S)NH₂ | 3,5-dimethyl-1H-pyrazol-4-yl-CO- |
| —C(=S)NH₂ | 3,5-dimethyl-1H-pyrazol-4-yl-CH₂- |
| —C(=S)NH₂ | 3-(trifluoromethyl)-5-methylisoxazol-4-yl-SO₂- |
| —C(=S)NH₂ | 3-(trifluoromethyl)-5-methyl-1H-pyrazol-4-yl-SO₂- |
| —C(=S)NH₂ | thiophen-2-yl-SO₂- |
| —C(=S)NH₂ | 5-chlorothiophen-2-yl-SO₂- |
| —C(=S)NH₂ | 2,4-dimethylthiazol-5-yl-SO₂- |
| —C(=S)NH₂ | 2-(methoxycarbonyl)thiophen-3-yl-SO₂- |

TABLE 6

(I-g)

[Structure: 5,6-bis(trifluoromethoxy)benzimidazole with R¹ at 2-position and Y-R² on N1]

| R¹ | R²—Y |
|---|---|
| —CN | 3,5-dimethylisoxazol-4-yl-SO₂- |

TABLE 6-continued
(I-g)
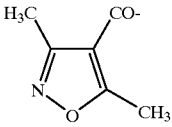
| R¹ | R²—Y |
|---|---|
| —CN | 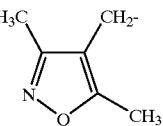 |
| —CN | 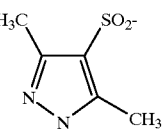 |
| —CN | 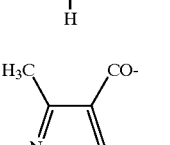 |
| —CN | 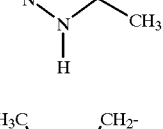 |
| —CN | 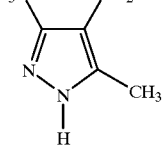 |
| —CN | 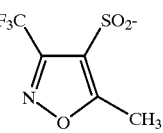 |
| —CN | 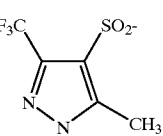 |
| —CN | 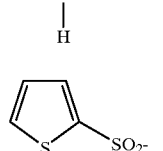 |
| —CN | 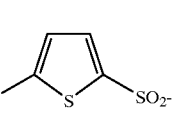 |
TABLE 6-continued
(I-g)
| R¹ | R²—Y |
|---|---|
| —CN | 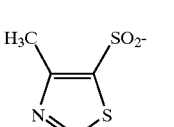 |
| —CN | 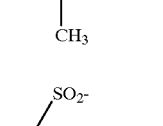 |
| 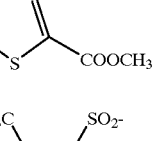 | 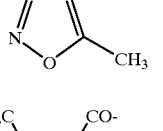 |
| 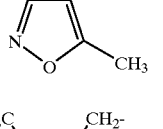 | 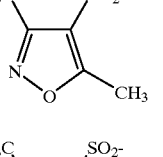 |
| 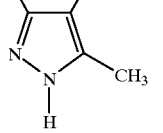 | 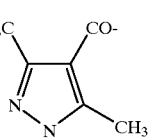 |
| 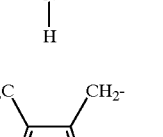 | 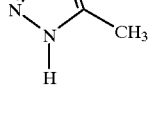 |
|  | |

TABLE 6-continued (I-g)

[Structure: benzimidazole with F3CO groups at 5,6 positions, R1 at 2-position, Y-R2 on N]

| R1 | R2—Y |
|---|---|
| —C(=S)—NH2 | 3-CF3-5-methyl-isoxazol-4-yl-SO2- |
| —C(=S)—NH2 | 3-CF3-5-methyl-1H-pyrazol-4-yl-SO2- |
| —C(=S)—NH2 | thiophen-2-yl-SO2- |
| —C(=S)—NH2 | 5-chloro-thiophen-2-yl-SO2- |
| —C(=S)—NH2 | 4-methyl-2-methyl-thiazol-5-yl-SO2- |
| —C(=S)—NH2 | 2-COOCH3-thiophen-3-yl-SO2- |

TABLE 7

(I-h)

[Structure: 3,5-dichloropyridin-2-yloxy-benzimidazole with R1 at 2-position, Y-R2 on N]

| R1 | R2—Y |
|---|---|
| —CN | 3-methyl-5-methyl-isoxazol-4-yl-SO2- |

TABLE 7-continued (I-h)

[Structure: 3,5-dichloropyridin-2-yloxy-benzimidazole with R1 at 2-position, Y-R2 on N]

| R1 | R2—Y |
|---|---|
| —CN | 3-methyl-5-methyl-isoxazol-4-yl-CO- |
| —CN | 3-methyl-5-methyl-isoxazol-4-yl-CH2- |
| —CN | 3-methyl-5-methyl-1H-pyrazol-4-yl-SO2- |
| —CN | 3-methyl-5-methyl-1H-pyrazol-4-yl-CO- |
| —CN | 3-methyl-5-methyl-1H-pyrazol-4-yl-CH2- |
| —CN | 3-CF3-5-methyl-isoxazol-4-yl-SO2- |
| —CN | 3-CF3-5-methyl-1H-pyrazol-4-yl-SO2- |
| —CN | thiophen-2-yl-SO2- |
| —CN | 5-chloro-thiophen-2-yl-SO2- |

TABLE 7-continued (I-h)

Structure: 3,5-dichloropyridin-2-yl-oxy-benzimidazole with R¹ at 2-position and Y—R² at N1.

| R¹ | R²—Y |
|---|---|
| —CN | 2,4-dimethylthiazole-5-SO₂- |
| —CN | 3-(COOCH₃)thiophene-2-SO₂- (shown as thiophene with SO₂- and COOCH₃) |
| —C(=S)—NH₂ | 3,5-dimethylisoxazole-4-SO₂- |
| —C(=S)—NH₂ | 3,5-dimethylisoxazole-4-CO- |
| —C(=S)—NH₂ | 3,5-dimethylisoxazole-4-CH₂- |
| —C(=S)—NH₂ | 3,5-dimethyl-1H-pyrazole-4-SO₂- |
| —C(=S)—NH₂ | 3,5-dimethyl-1H-pyrazole-4-CO- |
| —C(=S)—NH₂ | 3,5-dimethyl-1H-pyrazole-4-CH₂- |

TABLE 7-continued (I-h)

| R¹ | R²—Y |
|---|---|
| —C(=S)—NH₂ | 3-CF₃-5-methylisoxazole-4-SO₂- |
| —C(=S)—NH₂ | 3-CF₃-5-methyl-1H-pyrazole-4-SO₂- |
| —C(=S)—NH₂ | thiophene-2-SO₂- |
| —C(=S)—NH₂ | chloro-thiophene-SO₂- |
| —C(=S)—NH₂ | 2,4-dimethylthiazole-5-SO₂- |
| —C(=S)—NH₂ | 3-(COOCH₃)thiophene-2-SO₂- |

TABLE 8

(I-i)

Structure: 5-(trifluoromethyl)pyridin-2-yl-thio-benzimidazole with R¹ at 2-position and Y—R² at N1.

| R¹ | R²—Y |
|---|---|
| —CN | 3,5-dimethylisoxazole-4-SO₂- |

TABLE 8-continued (I-i)

[Structure: 5-(trifluoromethyl)pyridin-2-yl sulfanyl linked to benzimidazole with R¹ at position 2 and Y-R² at N]

| R¹ | R²—Y |
|---|---|
| —CN | 3,5-dimethylisoxazol-4-yl-CO- |
| —CN | 3,5-dimethylisoxazol-4-yl-CH₂- |
| —CN | 3,5-dimethyl-1H-pyrazol-4-yl-SO₂- |
| —CN | 3,5-dimethyl-1H-pyrazol-4-yl-CO- |
| —CN | 3,5-dimethyl-1H-pyrazol-4-yl-CH₂- |
| —CN | 3-trifluoromethyl-5-methylisoxazol-4-yl-SO₂- |
| —CN | 3-trifluoromethyl-5-methyl-1H-pyrazol-4-yl-SO₂- |
| —CN | cyclopentadienyl-SO₂- |
| —CN | 3-chlorocyclopentadienyl-SO₂- |
| —CN | 2,4-dimethylthiazol-5-yl-SO₂- |
| —CN | 2-methoxycarbonylthiophen-3-yl-SO₂- |
| —C(=S)NH₂ | 3,5-dimethylisoxazol-4-yl-SO₂- |
| —C(=S)NH₂ | 3,5-dimethylisoxazol-4-yl-CO- |
| —C(=S)NH₂ | 3,5-dimethylisoxazol-4-yl-CH₂- |
| —C(=S)NH₂ | 3,5-dimethyl-1H-pyrazol-4-yl-SO₂- |
| —C(=S)NH₂ | 3,5-dimethyl-1H-pyrazol-4-yl-CO- |
| —C(=S)NH₂ | 3,5-dimethyl-1H-pyrazol-4-yl-CH₂- |

TABLE 8-continued (I-i)

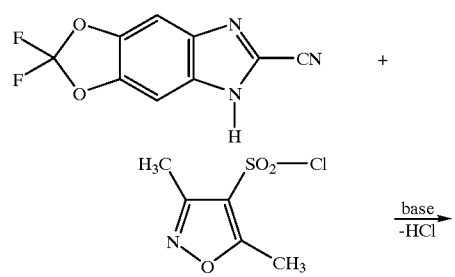

| R¹ | R²—Y |
|---|---|
| —C(=S)—NH₂ | 4-SO₂-(3-CF₃-5-CH₃-isoxazolyl) |
| —C(=S)—NH₂ | 4-SO₂-(3-CF₃-5-CH₃-1H-pyrazolyl) |
| —C(=S)—NH₂ | 2-SO₂-thienyl |
| —C(=S)—NH₂ | 5-SO₂-(2-Cl-thienyl) |
| —C(=S)—NH₂ | 5-SO₂-(2-CH₃-4-CH₃-thiazolyl) |
| —C(=S)—NH₂ | 3-SO₂-(2-COOCH₃-thienyl) |

If 2-cyano-6,6-difluoro-[1,3]dioxolo[4,5-f]benzimidazole and 3,5-dimethylisoxazole-4-sulphonyl chloride are used as starting materials, the course of the process according to the invention can be illustrated by the following equation:

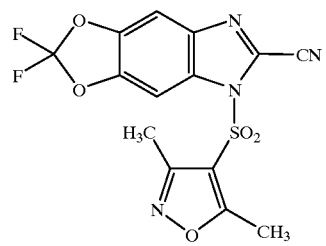

If 2-Cyano-6,6-difluoro-3-(3,5-dimethyl-isoxazolyl-4-sulphonyl)-[1,3]-dioxolo[4,5-f]benzimidazole is used as starting material and hydrogen sulphide is used as reaction component, the course of the process according to the invention can be illustrated by the following equation:

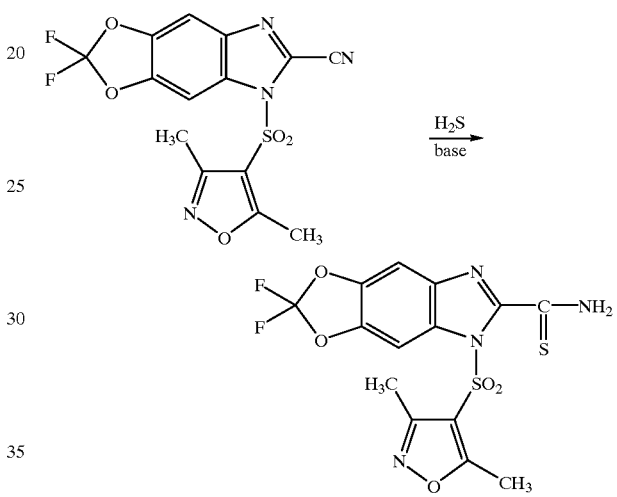

If 2-cyano-6,6-difluoro-3-(3,5-dimethyl-isoxazole-4-sulphonyl)-[1,3]-dioxolo-[4,5-f]benzimidazole is used as starting material and methyl mercaptan is used as reaction component, the course of the process according to the invention can be illustrated by the following equation:

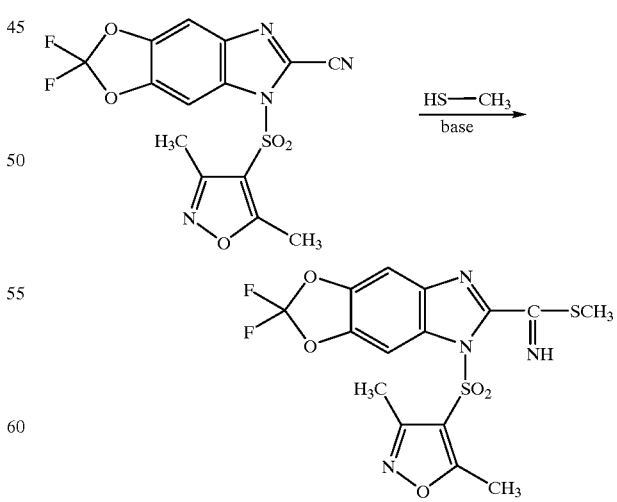

Formula (II) provides a general definition of the cyano-benzimidazoles required as starting materials for carrying out the first step of the process according to the invention.

In this formula, $X^1$, $X^2$, $X^3$ and $X^4$ each have those meanings which have already been mentioned in connection with the description of the compounds of the formula (I) according to the invention for these radicals.

The cyano-benzimidazoles of the formula (II) are known or can be prepared by methods known in principle (cf. DE-A 4 139 950, FR-A 2 572 412, EP-A 0 181 826, EP-A 0 517 476, EP-A 0 549 943 and EP-A 0 487 286).

Formula (III) provides a general definition of the halides further required as starting materials for carrying out the first step of the process according to the invention. In this formula, $R^2$ and Y each have those meanings which have already been mentioned in connection with the description of the compounds of the formula (I) according to the invention for these radicals. Hal represents chlorine or bromine.

The halides of the formula (III) are known or can be prepared by known methods.

Suitable diluents for carrying out the first step of the process according to the invention are all customary inert organic solvents. Preference is given to using aliphatic, cycloaliphatic and aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; furthermore ethers, such as diethyl ether, diisopropyl ether, dioxane, tetrahydrofuran or ethylene glycol dimethyl ether or ethylene glycol diethyl ether, furthermore ketones, such as acetone or butanone or methyl isobutyl ketone; nitrites such as acetonitrile, propionitrile or benzonitrile, or esters such as methyl acetate or ethyl acetate.

The first step of the process according to the invention is preferably carried out in the presence of an acid binder. Suitable acid binders are all customary inorganic or organic bases. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates such as sodium acetate, potassium acetate, calcium acetate, and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the first step of the process according to the invention, the reaction temperatures can be varied within a relatively wide range. In general, the process is carried out at temperatures between 0 and 150° C., preferably at temperatures between 20 and 120° C.

The first and the second step of the process according to the invention is generally carried out under atmospheric pressure. However, it is also possible to work under elevated or reduced pressure.

When carrying out the first step of the process according to the invention, generally 1.0 to 2.0 mol, preferably 1.0 to 1.3 mol, of a halide of the formula (III) and optionally 1.0 to 2.0 mol, preferably 1.0 to 1.3 mol, of an acid binder are employed per mole of a cyano-benzimidazole of the formula (II) in a diluent. Known processes are employed for carrying out the reaction and for the work-up and isolation of the reaction products (cf. also the preparation examples).

When carrying out the second step (variant a) of the process according to the invention, preferred acid binders are tertiary amines such as triethylamine.

When carrying out the second step of the process according to the invention (variant a), suitable diluents are all inert polar organic solvents. Preference is given to using amides, such as dimethyl formamide, and also ethers, such as diethyl ether or tetrahydrofuran, and aromatic amines, such as pyridine.

When carrying out the second step (variant a) of the process according to the invention, the reaction temperatures can also be varied within a relatively wide range. In general, this step is carried out at temperatures between −20° C. and +150° C., preferably between −10° C. and +80° C.

When carrying out the second step of the process according to the invention (variant a), an excess, preferably 2 to 5 mol, of hydrogen sulphide is employed per 1 mol of the benzimidazole derivative of the formula (I-a). Work-up is carried out by conventional methods.

Formula (IV) provides a general definition of the sulphur compounds required as reaction components for carrying out the second step (variant b) of the process according to the invention. In this formula, $R^6$ has those meanings already mentioned in connection with the description of the compounds of the formula (I) according to the invention for this radical.

When carrying out the second step (variant b) of the process according to the invention, preferred acid binders are alkali metal carbonates such as sodium carbonate or potassium carbonate.

Suitable diluents for carrying out the second step (variant b) of the process according to the invention are all customary polar aprotic solvents. Preference is given to using nitriles such as acetonitrile.

When carrying out the second step (variant b) of the process according to the invention, the reaction temperatures can also be varied within a relatively wide range. In general, this step is carried out at temperatures between −20° C. and +150° C., preferably between −10° C. and +80° C.

When carrying out the second step of the process according to the invention (variant b), an excess, preferably 2 to 5 mol, of the sulphur compound of the formula (IV) is employed per 1 mol of the benzimidazole derivative of the formula (I-a). Work-up is carried out by conventional methods.

The benzimidazole derivatives of the formula (I) can be converted into acid addition salts or metal salt complexes.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtering off, and, if appropriate, purified by washing with an inert organic solvent.

Suitable salts for the preparation of metal salt complexes of the compounds of the formula (I) are preferably those of metals which have already been mentioned in connection with the description of the metal salt complexes according to the invention as being preferred metal salts.

The metal salt complexes of the compounds of the formula (I) can be obtained in a simple manner by customary processes, for example by dissolving the metal salt in alcohol, for example ethanol, and adding the solution to the compounds of the formula (I). Metal salt complexes can be isolated in a known manner, for example by filtering off, and, if appropriate, purified by recrystallization.

The active compounds according to the invention have a strong microbicidal activity and can be employed for controlling undesirable microorganisms, such as fungi and bacteria, in crop protection and in the protection of materials.

The undesirable microorganisms include fungi, such as Plasmodiophoromycetes, Oomycetes, Chytridiomycetes, Zygomycetes, Ascomycetes, Basidiomycetes, Deuteromycetes and furthermore bacteria, such as Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species, such as *Xanthomonas oryzae;*

Pseudomonas species, such as *Pseudomonas lachrymans;*

Erwinia species, such as *Erwinia amylovora;*

Pythium species, such as *Pythium ultimum;*

Phytophthora species, such as *Phytophthora infestans;*

Pseudoperonospora species, such as *Pseudoperonospora humuli* or *Pseudoperonospora cubensis;*

Plasmopara species, such as *Plasmopara viticola;*

Peronospora species, such as *Peronospora pisi* or *P. brassicae;*

Erysiphe species, such as *Erysiphe graminis;*

Sphaerotheca species, such as *Sphaerotheca fuliginea;*

Podosphaera species, such as *Podosphaera leucotricha;*

Venturia species, such as *Venturia inaequalis;*

Pyrenophora species, such as *Pyrenophora teres* or *P. graminea* (conidia form: Drechslera, syn: Helminthosporium);

Cochliobolus species, such as *Cochliobolus sativus* (conidia form: Drechslera, syn: Helminthosporium);

Uromyces species, such as *Uromyces appendiculatus;*

Puccinia species, such as *Puccinia recondita;*

Tilletia species, such as *Tilletia caries;*

Ustilago species, such as *Ustilago nuda* or *Ustilago avenae;*

Pellicularia species, such as *Pellicularia sasakii;*

Pyricularia species, such as *Pyricularia oryzae;*

Fusarium species, such as *Fusarium culmorum;*

Botrytis species, such as *Botrytis cinerea;*

Septoria species, such as *Septoria nodorun;*

Leptosphaeria species, such as *Leptosphaeria nodorum;*

Cercospora species, such as *Cercospora canescens;*

Alternaria species, such as *Alternaria brassicae* and

Pseudocercosporella species, such as *Pseudocercosporella herpotrichoides.*

The good toleration, by plants, of the active compounds, at the concentrations required for controlling plant diseases, permits treatment of above-ground parts of plants, of vegetative propagation stock and seeds, and of the soil.

The active compounds according to the invention are particularly suitable for controlling diseases in fruit and vegetable growing, such as, for example against Venturia species, or for controlling cereal diseases, such as, for example Erysiphe, Cochliobolus, Pyrenophora, or Septoria species, or for controlling rice diseases, such as, for example, against the causative organism of rice blast (*Pyricularia oryzae*).

In materials protection the substances of the invention can be used to protect industrial materials against infestation and destruction by undesirable microorganisms.

The term industrial materials in the present context refers to nonliving materials which have been prepared for use in industry. Examples can be industrial materials which are to be protected by novel active substances against microbial alteration or destruction, adhesives, sizes, paper and card, textiles, leather, wood, coating compositions and plastics articles, cooling lubricants and other materials which can be infested or decomposed by microorganisms. In the context of the materials to be protected mention may also be made of parts of production plants, for example cooling water circuits, which may be adversely affected by reproduction of microorganisms. Preferred industrial materials in the context of the present invention are adhesives, sizes, papers and cards, leather, wood, coating compositions, cooling lubricants and heat transfer fluids, especially wood.

Examples of microorganisms which can bring about degradation or an alteration in the industrial materials are bacteria, fungi, yeasts, algae and slime organisms. The active substances according to the invention preferably act against fungi, especially mould fungi, wood-discolouring and wood-destroying fungi (Basidiomycetes) and also against slime organisms and algae.

By way of example, mention may be made of the following genera:

Alternaria, such as *Alternaria tenuis,*

Aspergillus, such as *Aspergillus niger,*

Chaetomium, such as *Chaetomium globosum,*

Coniophora, such as *Coniophora puetana,*

Lentinus, such as *Lentinus tigrinus,*

Penicillium, such as *Penicillium glaucum,*

Polyporus, such as *Polyporus versicolor,*

Aureobasidium, such as *Aureobasidium pullulans,*

Sclerophoma, such as *Sclerophoma pityophila,*

Trichoderma, such as *Trichoderma viride,*

Escherichia, such as *Escherichia coli,*

Pseudomonas, such as *Pseudomonas aeruginosa,*

Staphylococcus, such as *Staphylococcus aureus.*

In addition, the active compounds according to the invention are suitable for controlling animal pests, preferably arthropods and nematodes, in particular insects and arachnids encountered in agriculture, in forests, in the protection of stored goods and of materials and in the field of hygiene. They are active against normally sensitive and resistant species and against all or some development stages.

The cyanobenzimidazoles of the formula (II) are also fungicidally active.

Depending on their respective physical and/or chemical properties, the active substances can be converted into customary formulations, such as solutions, emulsions, suspensions, powders, foams, pastes, granules, aerosols, very fine capsules in polymeric substances and in coating compositions for seed, and also ULV cold-mist and warm-mist formulations.

These formulations are prepared in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents such as alcohols can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polypxyethylene fatty alcohol ethers, for example alkylaryl polyglycol ethers, alkylsulphonates, alkyl sulphates, arylsulphonates as well as protein hydrolysates; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

The active compounds according to the invention, when used in crop protection, can be used in the formulations as a mixture with known fungicides, bactericides, acaricides, nematicides or insecticides, for example so as to widen the spectrum of action or to prevent the build up of resistance.

Suitable components for the mixtures are, for example, the following substances:

Fungicides:
  2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxyphenyl) acetamide; 8-hydroxyquinoline sulphate; methyl (E)-2-{2-[6-(2-cyanophenoxy)pyrimidin-4-yloxy]-phenyl}-3-methoxyacrylate; methyl (E)-methoxyimino [alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichiamide, tricyclazole, tridemorph, triflumizole, triforine, triticonazole, validamycin A, vinclozolin, zineb, ziram.

Bactericides:
  bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicides:
  abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocytirin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mervinphos, mesulfenfos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrichlophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides, or with fertilizers and growth regulators, is also possible.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the concentrations of active substance in the use forms can be varied within a relatively large range: they are in general between 1 and 0.0001% by weight, preferably between 0.5 and 0.001% by weight.

In the treatment of seed, amounts of active substance of from 0.001 to 50 g per kilogram of seed, preferably from 0.01 to 10 g, are generally required.

In the case of the treatment of soil, active-substance concentrations of from 0.00001 to 0.1% by weight, preferably from 0.0001 to 0.02% by weight, are required at the site of action.

The compositions used for protecting industrial materials comprise the active substances in an amount of in general from 1 to 95%, preferably from 10 to 75%.

The concentrations in which the novel active substances are applied depend on the nature and on the incidence of the microorganisms to be combated and on the composition of the material to be protected. The optimum amount for use can be determined by means of test series. In general, the use concentrations are in the range from 0.001 to 5% by weight, preferably from 0.05 to 1.0% by weight, based on the material to be protected.

The effectiveness and the spectrum of action of the active substances to be used in materials protection in accordance with the invention and of the compositions, concentrates or, very generally, formulations which can be prepared therefrom can be increased by adding, if desired, further antimicrobially active compounds, fingicides, bactericides, herbicides, insecticides or other active substances to increase the spectrum of action or to achieve particular effects, for example additional protection against insects. These mixtures may possess a broader spectrum of action than the compounds according to the invention.

In many instances, this results in synergistic effects, i.e. the spectrum of activity of the mixture is superior to the activity of the individual components. Particularly advantageous mixing partners are, for example, the following compounds:

Sulphenamides such as dichlofluanide (Euparene), tolylfluanide (Methyleuparene), folpet, fluorfolpet;

Benzimidazoles such as carbendazim (MBC), benomyl, fuberidazole, thiabendazole or their salts;

Thiocyanates such as thiocyanatomethylthiobenzothiazole (TCMTB), methylene bisthiocyanate (MBT);

Quaternary ammonium compounds such as benzyldimethyltetradecylammonium chloride, benzyl-dimethyldodecyl-ammonium chloride, dodecyl-dimethyl-ammonium chloride;

Morpholine derivatives such as $C_{11}$–$C_{14}$-4-alkyl-2,6-dimethyl-morpholine homologues (tridemorph), (±)-cis-4-[tert-butylphenyl]-2-methylpropyl]-2,6-dimethylmorpholine (fenpropimorph), Falimorph;

Phenols such as o-phenylphenol, tribromophenol, tetrachlorophenol, pentachlorophenol, 3-methyl-4-chlorophenol, dichlorophene, chlorophene or their salts;

Azoles such as triadimefon, triadimenol, bitertanol, tebucanozole, propiconazole, azaconazole, hexaconazole, prochloraz, cyproconazole, 1-(2-chlorophenyl)-2-(1-chlorocyclopropyl)-3-(1,2,4-triazol-1-yl)-propan-2-ol or 1-(2-chlorophenyl)-2-(1,2,4-triazol-1-yl-methyl)-3,3-dimethyl-butan-2-ol.

Iodopropargyl derivatives such as iodopropargyl butylcarbamate (IPBC), iodopropargyl chlorophenylformal, iodopropargyl phenylcarbamate, iodopropargyl hexylcarbamate, iodopropargyl cyclohexylcarbamate, iodopropargyloxyethyl phenylcarbamate;

Iodine derivatives such as diiodomethyl-p-aryl sulphones, for example diiodomethyl-p-tolyl sulphone;

Bromine derivatives such as bromopol;

Isothiazolines such as N-methylisothiazolin-3-one, 5-chloro-N-methylisothiazolin-3-one, 4,5-dichloro-N-octylisothiazolin-3-one, N-octylisothiazolin-3-one (octilinone);

Benzisothiazolinones, cyclopenteneisothazolines;

Pyridines such as 1-hydroxy-2-pyridinthione (and their Na, Fe, Mn and Zn salts), tetrachloro-4-methylsulphonylpyridine;

Metal soaps such as the naphthenates, octoactes, 2-ethylhexanoates, oleates, phosphates and benzoates of tin, copper and zinc, oxides such as TBTO, $Cu_2O$, CuO, ZnO;

Organic tin compounds such as tributyltin naphthenate and tributyltin oxide;

Dialkyl dithiocarbamates such as the Na and Zn salts of dialkyldithiocarbamates, tetramethyltiurami disulphide (TMTD);

Nitriles such as 2,4,5,6-tetrachloroisophthalonitrile (chlorothalonil) and other microbicides having an activated halogen group, such as Cl—Ac, MCA, tectamer, bromopol, bromidox;

Benzothiazoles such as 2-mercaptobenzothiazole; see above dazomet;

Quinolines such as 8-hydroxyquinoline;

Formaldehyde-releasing compounds such as benzyl alcohol mono(poly)hemiformal, oxazolidines, hexahydros-triazines, N-methylolchloroacetamide;

Tris-N-(cyclohexyldiazeniumdioxy)-aluminium, N-(cyclohexyldiazeniumdioxy)-tributyltin or K salts, bis-(N-cyclohexyl)diazinium-(dioxy-copper or aluminium).

Preference is given to using the following insecticides:

Phosphoric esters such as azinphos-ethyl, azinphos-methyl, 1-(4-chlorophenyl)-4-(O-ethyl, S-propyl) phosphoryloxypyrazol (TIA-230), chlorpyrifos, coumaphos, demeton, demeton-S-methyl, diazinon, dichlorfos, dimethoate, ethoprophos, etrimfos, fenitrothion, fention, heptenophos, parathion, parathion-methyl, phosalone, phoxim, pirimiphos-ethyl, pirimiphos-methyl, profenofos, prothiofos, sulprofos, triazophos and trichlorphon.

Carbamates such as aldicarb, bendiocarb, BPMC (2-(1-methylpropyl)phenyl methylcarbamate), butocarboxim, butoxycarboxim, carbaryl, carbofuran, carbosulfan, cloethocarb, isoprocarb, methomyl, oxamyl, pirimicarb, promecarb, propoxur and thiodicarb.

Pyrethroids such as allethrin, alphamethrin, bioresmethrin, byfenthrin (FMC 54800), cycloprothrin, cyfluthrin, decamethrion, cyhalothrin, cypermethrin, deltamethrin, alphacyano-3-phenyl-2-methylbenzyl-2,2-dimethyl-3-(2-chloro-2-trifluoromethylvinyl) cyclopropanecarboxylate, fenpropathrin, fenfluthrin, fenvalerate, flucythrinate, flumethrin, fluvalinate, permethrin and resmethrin; nitroimino and nitromethylene compounds such as 1-[(6-chloro-3-pyridinyl)-methyl]-4,5-dihydro-N-nitro-1H-imidazol-2-amine (imidachloprid).

Organosilicon compounds, preferably dimethyl(phenyl) silylmethyl 3-phenoxybenzyl ethers, such as, for example, dimethyl-(4-ethoxyphenyl)-silylmethyl 3-phenoxybenzyl ether, or dimethyl(phenyl)-silylmethyl 2-phenoxy-6-pyridylmethyl ethers, such as, for example, dimethyl(9-ethoxyphenyl)-silylmethyl 2-phenoxy-6-pyridylmethyl ether, or (phenyl)[3-(3-phenoxyphenyl)propyl](dimethyl)-silanes, such as, for example, (4-ethoxyphenyl)-[3(4-fluoro-3-phenoxyphenyl)-propyl]dimethylsilane.

Further suitable active compounds are algicides, molluscicides and active compounds against sea animals which colonize, for example, ship bottom paints.

The preparation and the use of the active compounds according to the invention is illustrated by the examples below.

PREPARATION EXAMPLES

Example 1

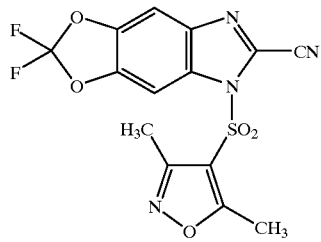

At room temperature, a mixture of 3.4 g (15 mmol) of 2-cyano-6,6-difluoro-[1,3]dioxolo[4,5-f]benzimidazole and 80 ml of absolute tetrahydrofuran is admixed with stirring with 0.45 g (15 mmol) of sodium hydride (80% pure) and then stirred at room temperature for 10 minutes. 2.9 g (15 mmol) of 3,5-dimethylisoxazolyl-4-sulphonyl chloride is then added and the mixture is stirred at 60° C. for 18 hours. For work-up, the reaction mixture is poured into 200 ml of water. The resulting mixture is extracted three times with 80 ml of methylene chloride each time. The combined organic phases are dried over sodium sulphate and concentrated under reduced pressure. The remaining residue is chromatographed over silica gel using diethyl ether as eluent. In this manner, 1.4 g (24% of theory) of 2-cyano-6,6-difluoro-3-(3,5-dimethyl-isoxazolyl-4-sulphonyl)-[1,3]dioxolo[4,5-f] benzimidazole in the form of a yellow solid of melting point 166 to 170° C. are obtained.

Example 2

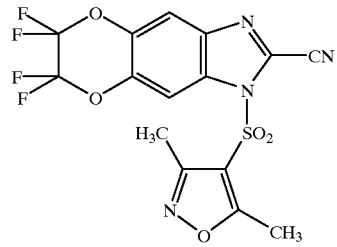

At room temperature, a mixture of 0.30 g (10 mmol) of sodium hydride (80% pure) and 40 ml of absolute tetrahydrofuran is admixed with stirring with 2.7 g (10 mmol) of 2-cyano-6,6,7,7-tetrafluoro[1,4]-dioxino[2,3-f] benzimidazole and then stirred at room temperature for 10 minutes. 2.9 g (15 mmol) of 3,5-dimethylisoxazolyl-4-sulphonyl chloride are then added and the mixture is stirred at 60° C. for 4 hours. For work-up, the reaction mixture is poured into 200 ml of water. The resulting mixture is extracted three times with 80 ml of methylene chloride each time. The combined organic phases are dried over sodium sulphate and concentrated under reduced pressure. The remaining residue is recrystallized from 20 ml of a mixture consisting of equal amounts of diethyl ether and petroleum ether. In this manner, 1.9 g (44% of theory) of 2-cyano-6, 6,7,7-tetrafluoro-3-(3,5-dimethyl-isoxazolyl-4-sulphonyl)-[1,4]-dioxino[2,3-f]benzimidazole in the form of a solid of melting point 180 to 185° C. are obtained.

Example 3

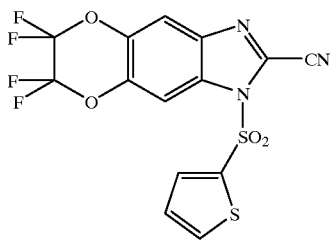

At room temperature, a mixture of 0.30 g (10 mmol) of sodium hydride (80% pure) and 40 ml of absolute tetrahydrofuran is admixed with stirring with 2.7 g (10 mmol) of 2-cyano-6,6,7,7-tetrafluoro[1,4]-dioxino[2,3-f] benzimidazole and then stirred at room temperature for 10 minutes. 2.2 g (12 mmol) of thiophene-2-sulphonyl chloride are then added and the mixture is stirred at 60° for 18 hours. For work-up, the reaction mixture is poured into 200 ml of water. The resulting precipitate is filtered off and dissolved in 50 ml of ethyl acetate. The solution is dried over sodium sulphate and then concentrated under reduced pressure. The remaining residue is stirred with 20 ml of petroleum ether. The resulting precipitate is filtered off and dried. In this manner, 1.9 g (49% of theory) of 2-cyano-6,6,7,7-tetrafluoro-3-(thienyl-2-sulphonyl)-[1,4]-dioxino[2,3-f]-benzimidazole in the form of a yellow solid of melting point 180 to 184° are obtained.

Using the abovementioned methods, the compounds of the formula

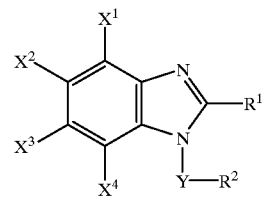

(I)

listed in Table 9 were also prepared.

TABLE 9

| Ex. No. | $X^1$ | $X^2$ | $X^3$ | $X^4$ | —Y—$R^2$ | $R^1$ | Melting point (° C.) |
|---|---|---|---|---|---|---|---|
| 4 | Br | H | $CF_3$ | H | H₃C-isoxazole-SO₂- with CH₃ | —CN | 145–149 |
| 5 | Br | H | $CF_3$ | H | Cl-thiophene-SO₂- | —CN | 117–121 |
| 6 | Br | H | $CF_3$ | H | Br,Br-thiophene-SO₂- | —CN | 217–220 |
| 7 | H | —O—CClF—CClF—O— | | H | Cl-thiophene-SO₂- | —CN | 115–119 |
| 8 | H | —O—CF₂—O— | | H | H₃C-isoxazole-SO₂- | —CN | 166–168 |
| 9 | H | —O—CF₂—O— | | H | H₃C-isoxazole-CH₂- with CH₃ | —CN | 161–165 |
| 10 | H | —O—CF₂—CF₂—O— | | H | H₃C-isoxazole-CH₂- with CH₃ | —CN | 155–160 |

TABLE 9-continued

| Ex. No. | $X^1$ | $X^2$ | $X^3$ | $X^4$ | —Y—$R^2$ | $R^1$ | Melting point (° C.) |
|---|---|---|---|---|---|---|---|
| 11 | H | —O—$CF_2$—$CF_2$—O— | | H | 3,5-dimethylisoxazol-4-yl-$SO_2$- | —CN | 65–68 |
| 12 | H | —O—$CF_2$—O— | | H | thiophen-2-yl-$SO_2$- | —CN | 160–164 |
| 13 | H | —O—$CF_2$—$CF_2$—O— | | H | 5-chlorothiophen-2-yl-$SO_2$- | —CN | 178–180 |
| 14 | H | —O—$CF_2$—O— | | H | 5-chloro-1,3-dimethylpyrazol-4-yl-$SO_2$- | —CN | 171–176 |
| 15 | H | —O—$CF_2$—O— | | H | 5-chlorothiophen-2-yl-$SO_2$- | —CN | 121–124 |
| 16 | H | —O—$CF_2$—$CF_2$—O— | | H | 5-chloro-1,3-dimethylpyrazol-4-yl-$SO_2$- | —CN | 220–225 |
| 17 | H | —O—$CF_2$—$CF_2$—O— | | H | 4,5-dibromothiophen-2-yl-$SO_2$- | —CN | >220 |
| 18 | H | —O—$CF_2$—O— | | H | 4,5-dibromothiophen-2-yl-$SO_2$- | —CN | >220 |
| 19 | H | —O—$CF_2$—O— | | H | 2-(methoxycarbonyl)thiophen-3-yl-$SO_2$- | —CN | 135–140 |
| 20 | H | —O—$CF_2$—$CF_2$—O— | | H | 2-(methoxycarbonyl)thiophen-3-yl-$SO_2$- | —CN | 124–130 |

TABLE 9-continued
| Ex. No. | X¹ | X² | X³ | X⁴ | —Y—R² | R¹ | Melting point (° C.) |
|---|---|---|---|---|---|---|---|
| 21 | H | —O—CFCl—CFCl—O— | | H | 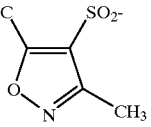 | —CN | 180–183 |
| 22 | Br | H | CF₃ | H | 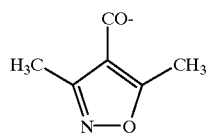 | —CN | 161–164 |
| 23 | H | —OCF₂CF₂O— | | H | 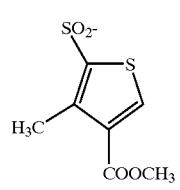 | —CN | 148–151 |
| 24 | H | —O—CF₂—O— | | H | 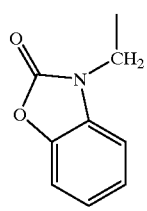 | —CN | 155–158 |
| 25 | H | —O—CF₂—O— | | H | 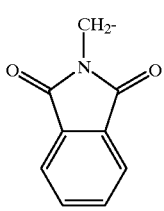 | —CN | <220 |
| 26 | H | —OCF₂—O— | | H | 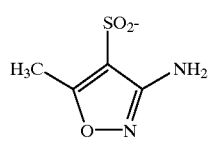 | —CN | 203–208 |
| 27 | H | —OCF₂—CHF—O— | | H | 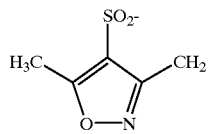 | —CN | 149–153 |
| 28 | H | —OCF₂—O— | | H | 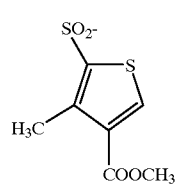 | —CN | 138–141 |
| 29 | H | —OCF₂O— | | H | 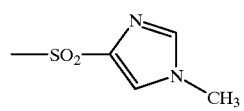 | —CN | 210–215 |

TABLE 9-continued

| Ex. No. | $X^1$ | $X^2$ | $X^3$ | $X^4$ | —Y—$R^2$ | $R^1$ | Melting point (° C.) |
|---|---|---|---|---|---|---|---|
| 30 | H | —O—$CF_2CF_2$O— | | H | ![SO2-imidazole-CH3] | —CN | 186–190 |
| 31 | H | —$OCF_2$O— | | H | ![CO-cyclopentadiene-H3C-CH3] | —CN | 150–154 |
| 32 | H | —$OCF_2CF_2$O— | | H | ![H3C-thiazole-SO2- NH-COCH3] | —CN | 210–214 |

USE EXAMPLES

In the following use examples, the compounds listed below were used as comparison substances.

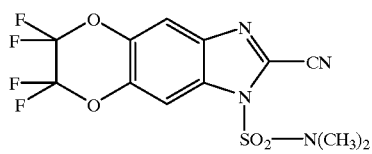

(A)

2-Cyano-1-dimethylaminosulphonyl-6,6,7,7-tetrafluoro-[1,4]dioxino[2,3-f]benzimidazole

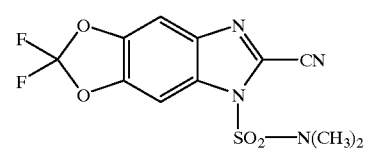

(B)

2-Cyano-6,6-difluoro-1-dimethylaminosulphonyl-[1,3]dioxolo[4,5-f]benzimidazole (Known from EP-A 0 517 476 and DE-A 4 139 950).

Example A

Venturia Test (apple)/Protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound to run-off point. After the spray coating has dried on, the plants are inoculated with an aqueous suspension of conidia of the causative organism of apple scab (*Venturia inaequalis*) and then remain in an incubation cupboard at 20° C. and 100% relative atmospheric humidity for 1 day.

The plants are then placed in a greenhouse at 20° C. and a relative atmospheric humidity of about 70%.

Evaluation is carried out 12 days after the inoculation. 0% means an efficacy corresponding to that of the control, 100% means that no infestation is observed.

In this test, the compounds of Examples 1 to 3 exhibited an efficacy of more than 50% at an active compound concentration of 10 ppm in the spray liquor, whereas comparison substance (A) showed an efficacy of 43% and comparison substance (B) showed no activity.

TABLE A

Venturia test (apple)/protective

| Active compounds | Efficacy in %, based on the untreated control, at an active compound concentration of 10 ppm |
|---|---|

Known from EP-A 0 517 476

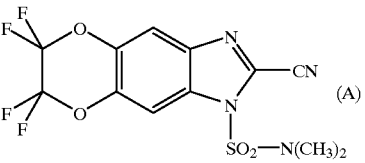

According to the invention:

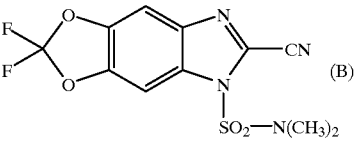

Example B

Phytophthora Test (tomato)/Protective

Solvent: 4.7 parts by weight of acetone

Emulsifier: 0.3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound to run-off point. After the spray coating has dried on, the plants are inoculated with an aqueous suspension of spores of *Phytophthora infestans*.

The plants are placed in an incubation cupboard at 100% relative atmospheric humidity and about 20° C.

Evaluation is carried out 3 days after the inoculation. 0% means an efficacy corresponding to that of the control, whereas an efficacy of 100% means that no infestation was observed.

Active compounds, active compound concentrations and test results are listed in the table below.
TABLE B
Phytophthora test (tomato)/protective
| Active compounds | Efficacy in %, based on the untreated control, at an active compound concentration of 100 ppm |
|---|---|
According to the invention:
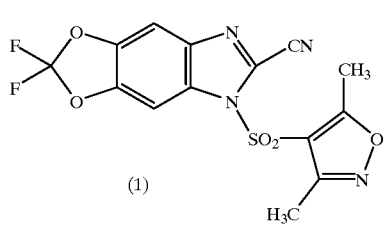
(1)                                                                                              100
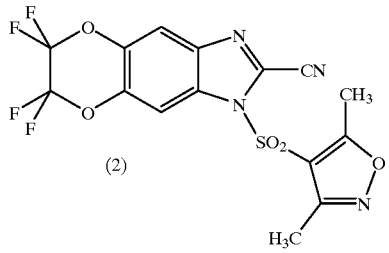
(2)                                                                                             97
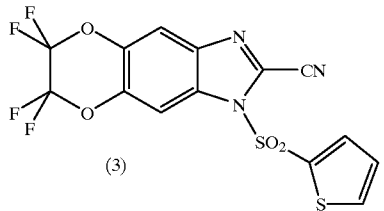
(3)                                                                                             94
According to the invention:
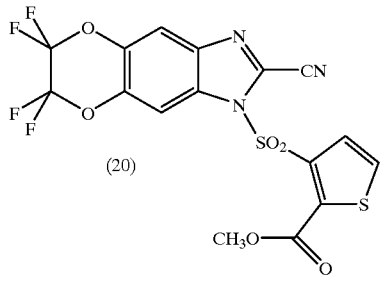
(20)                                                                                    82
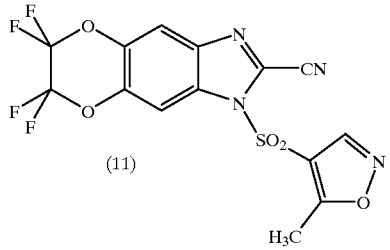
(11)                                                                                  64

TABLE B-continued
Phytophthora test (tomato)/protective
| Active compounds | Efficacy in %, based on the untreated control, at an active compound concentration of 100 ppm |
|---|---|
| 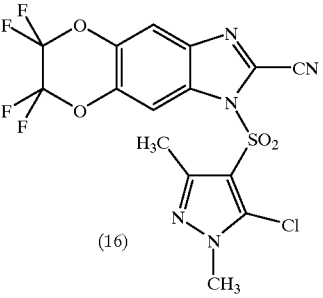 (16) | 94 |
| According to the invention: | |
| 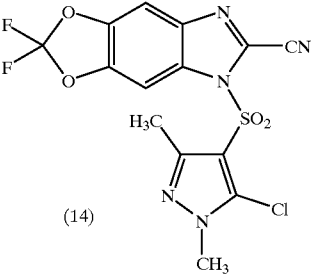 (14) | 94 |
| 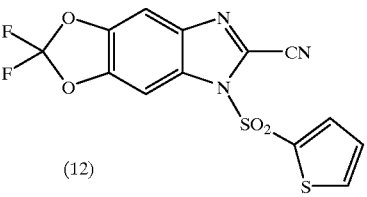 (12) | 94 |
| 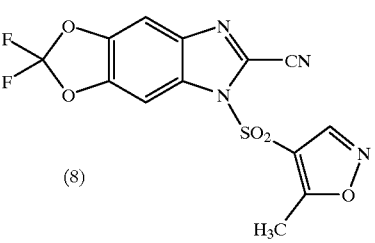 (8) | 96 |
| According to the invention: | |
| 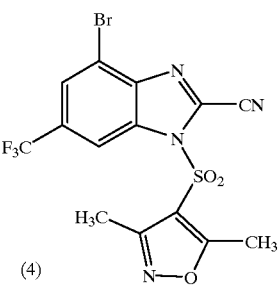 (4) | 74 |

TABLE B-continued

Phytophthora test (tomato)/protective

| Active compounds | Efficacy in %, based on the untreated control, at an active compound concentration of 100 ppm |
|---|---|
| 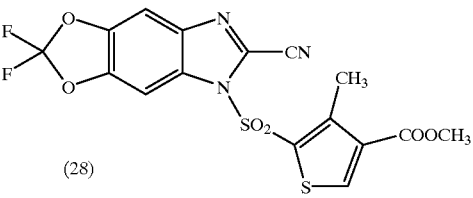 (28) | 97 |
| 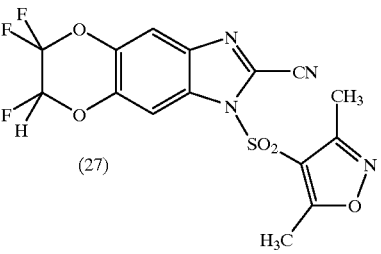 (27) | 97 |

Example C
Plasmopara Test (vines)/Protective

Solvent: 4.7 parts by weight of acetone

Emulsifier: 0.3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound to run-off point. After the spray coating has dried on, the plants are inoculated with an aqueous suspension of spores of *Plasmopara viticola* and then remain in a humidity chamber at 20–22° C. and 100% relative atmospheric humidity for 1 day. The plants are subsequently placed in a greenhouse at 21° C. and 90% atmospheric humidity for 5 days. The plants are then moistened and placed in a humidity chamber for 1 day.

Evaluation is carried out 6 days after the inoculation. 0% means an efficacy corresponding to that of the control, whereas an efficacy of 100% means that no infestation is observed.

Active compounds, active compound concentrations and test results are listed in the table below.

TABLE C

Plasmopara test (vines)/protective

| Active compounds | Efficacy in %, based on the untreated control, at an active compound concentration of 100 ppm |
|---|---|
| According to the invention: | |
| 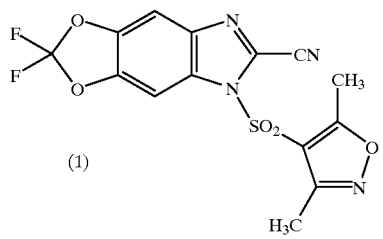 (1) | 100 |

TABLE C-continued

Plasmopara test (vines)/protective

| Active compounds | Efficacy in %, based on the untreated control, at an active compound concentration of 100 ppm |
|---|---|
| (2) | 100 |
| (3) | 80 |
| (20) | 100 |
| (11) | 100 |
| (16) | 74 |

TABLE C-continued

Plasmopara test (vines)/protective

| Active compounds | Efficacy in %, based on the untreated control, at an active compound concentration of 100 ppm |
|---|---|
| 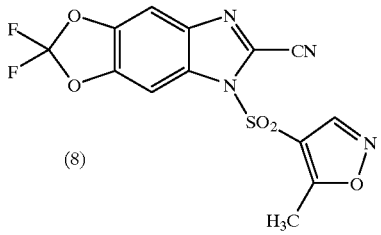 (8) | 100 |
| 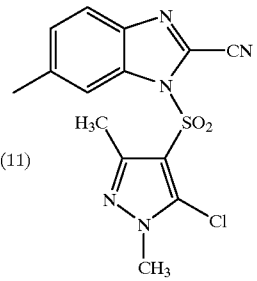 (11) | 95 |
| 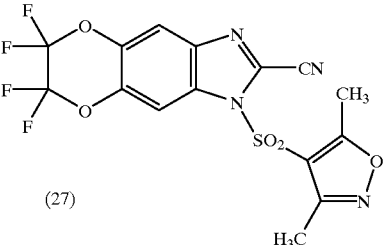 (27) | 100 |

What is claimed is:

1. A benzimidazole derivative of the formula

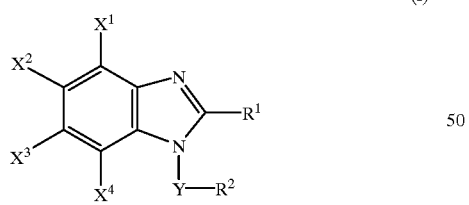

in which $X^1$, $X^2$, $X^3$ and $X^4$ independently of one another each represent hydrogen, fluorine, chlorine, bromine, iodine, cyano, nitro, straight-chain or branched alkyl having 1 to 8 carbon atoms, straight-chain or branched halogenoalkyl having 1 to 6 carbon atoms and 1 to 13 identical or different halogen atoms, straight-chain or branched alkoxy having 1 to 8 carbon atoms, straight-chain or branched halogenoalkoxy having 1 to 6 carbon atoms and 1 to 14 identical or different halogen atoms, straight-chain or branched alkylthio having 1 to 8 carbon atoms, straight-chain or branched halogenoalkylthio having 1 to 6 carbon atoms and 1 to 13 identical or different halogen atoms, straight-chain or branched alkylsulphinyl having 1 to 8 carbon atoms, straight-chain or branched halogenoalkylsulphonyl having 1 to 6 carbon atoms and 1 to 13 identical or different halogen atoms, straight-chain or branched alkylsulphonyl having 1 to 8 carbon atoms, straight-chain or branched halogenoalkylsulphonyl having 1 to 6 carbon atoms and 1 to 13 identical or different halogen atoms, cycloalkyl having 3 to 6 carbon atoms which is optionally mono- to pentasubstituted by identical or different substitutents from the group consisting of halogen and alkyl having 1 to 4 carbon atoms, represent hydroxycarbonyl, alkylcarbonyl having 1 to 6 carbon atoms in the straight-chain or branched alkyl moiety, alkoxycarbonyl having 1 to 6 carbon atoms in the straight-chain or branched alkoxy moiety, cycloalkylcarbonyl having 3 to 6 carbon atoms in the cycloalkyl moiety, $X^2$ and $X^3$ together also represent an alkylene chain having 3 or 4 members which is optionally mono- to hexasubstituted by halogen, alkyl having 1 to 4 carbon atoms and/or halogenoalkyl having 1 to 4 carbon atoms and 1 to 9 halogen atoms and in which one or two (non-adjacent) carbon atoms may be replaced by oxygen atoms, $R^1$ represents cyano or the groupings,

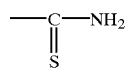

or

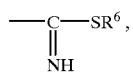

$R^6$ represents straight-chain or branched alkyl having 1 to 4 carbon atoms, straight-chain or branched halogenoalkyl having 1 to 4 carbon atoms and 1 to 9 identical or different halogen atoms or represents benzyl which is optionally mono- to trisubstituted by identical or different substitutents from the group consisting of halogen and halogenoalkyl having 1 or 2 carbon atoms and 1 to 5 identical or different halogen atoms, $R^2$ represents a pyrazolyl group, it being possible for this group to be mono- or disubstituted by identical or different substitutents from the group consisting of halogen, cyano, nitro, hydroxyl, amino, formyl, carboxy, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 6 carbonatoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, alkylcarbonylamino having 1 to 4 carbon atoms in the alkyl group, hydroxyiminoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety and halogenoalkylcarbonyloxy having 1 to 4 carbon atoms in the halogenoalkyl group and 1 to 5 identical or different halogen atoms, and Y represents a direct bond, represents, $CH_2$—$CH_2$, CO, $SO_2$, —CO—O— or —SO—O—, where in the case of the last two groups the carbon atom or the sulphur atom is linked to the nitrogen atom of the imidazole ring.

2. A benzimidazole derivative according to claim 1, which has the formula (14)

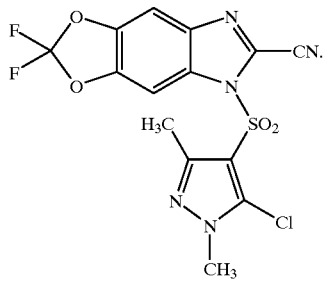

3. A microbicidal composition comprising a microbicidally effective amount of the benzimidazole derivative according to claim 1 and inert carrier.

4. A method for the control of undesired microorganisms, which method comprises applying to such microorganisms or their habitat a microbicidally effective amount of the benzimidazole derivative according to claim 1.

5. A microbicidal composition comprising a microbicidally effective amount of the benzimidazole derivative according to claim 2 and an inert carrier.

6. A method for the control of undesired microorganisms, which method comprises applying to such microorganisms or to their habitat a microbicidally effective amount of the benzimidazole derivative according to claim 2 and an inert carrier.

* * * * *

UNITED STATES PATENT AND TRADEMARK OFFICE
CERTIFICATE OF CORRECTION

PATENT NO.      : 6,235,765 B1
DATED           : May 22, 2001
INVENTOR(S)     : Lutz Assmann et al.

It is certified that error appears in the above-identified patent and that said Letters Patent is hereby corrected as shown below:

Title page,
Item [62], Related U.S. Application Data, please delete the caption and insert the following:

-- Division of U.S. Ser. No. 09/227,809, filed Jan. 11, 1999, now U.S. Pat. No. 6,080,776, issued Jun. 27, 2000, which is a divisional of U.S. Ser. No. 08/930,767, filed Oct. 3, 1997, now U.S. Pat. No. 5,925,663, issued Jul. 20, 1999, which is a 371 of PCT/EP96/01435 filed April 1, 1996. --

Column 1,
Delete lines 1-8, and insert the following:

-- This application is a divisonal of U.S. Ser. No. 09/227,809, filed Jan. 11, 1999, now U.S. Pat. No. 6,080,776, issued Jun. 27, 2000, which is a divisional of U.S. Ser. No. 08/930,767, filed Oct. 3, 1997, now U.S. Pat. No. 5,925,663, issued Jul. 20, 1999, which is a 371 of PCT/EP96/01435 filed April 1, 1996. --

Signed and Sealed this

Eighth Day of July, 2003

JAMES E. ROGAN
*Director of the United States Patent and Trademark Office*